US012215872B2

(12) United States Patent
Sun et al.

(10) Patent No.: US 12,215,872 B2
(45) Date of Patent: Feb. 4, 2025

(54) AUTO DETECTION SYSTEM FOR COOKING ASSISTANCE AND HAIR DRYER WITH THERMAL DETECTION

(71) Applicant: PixArt Imaging Inc., Hsin-Chu County (TW)

(72) Inventors: Chih-Ming Sun, Hsin-Chu County (TW); Ming-Han Tsai, Hsin-Chu County (TW); Chiung-Wen Lin, Hsin-Chu County (TW); Po-Wei Yu, Hsin-Chu County (TW); Wei-Ming Wang, Hsin-Chu County (TW); Sen-Huang Huang, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 0 days.

(21) Appl. No.: 18/224,288

(22) Filed: Jul. 20, 2023

(65) Prior Publication Data

US 2023/0358412 A1    Nov. 9, 2023

Related U.S. Application Data

(63) Continuation of application No. 17/584,755, filed on Jan. 26, 2022, now Pat. No. 11,754,293, which is a continuation of application No. 16/818,442, filed on Mar. 13, 2020, now Pat. No. 11,280,500, which is a continuation-in-part of application No. 16/458,626, filed on Jul. 1, 2019, now Pat. No. 10,871,394.

(60) Provisional application No. 62/887,740, filed on Aug. 16, 2019, provisional application No. 62/714,132, filed on Aug. 3, 2018.

(51) Int. Cl.
| | |
|---|---|
| *F24C 15/20* | (2006.01) |
| *A61F 13/42* | (2006.01) |
| *B66B 5/00* | (2006.01) |
| *G01J 5/00* | (2022.01) |
| *G01J 5/10* | (2006.01) |

(52) U.S. Cl.
CPC .......... *F24C 15/2042* (2013.01); *A61F 13/42* (2013.01); *B66B 5/0012* (2013.01); *G01J 5/0025* (2013.01); *G01J 5/10* (2013.01); *A61F 2013/421* (2013.01); *G01J 2005/0077* (2013.01); *G01J 2005/106* (2013.01)

(58) Field of Classification Search
CPC ..... F24C 15/2042; A61F 13/42; B66B 5/0012
See application file for complete search history.

(56) References Cited

U.S. PATENT DOCUMENTS

| | | | | |
|---|---|---|---|---|
| 10,810,860 B1 * | 10/2020 | Eubanks | ................. | G01J 5/026 |
| 2013/0171304 A1 * | 7/2013 | Huntley | ................. | G06Q 50/00 |
| | | | | 434/127 |
| 2014/0234496 A1 * | 8/2014 | Siegel | ..................... | F23N 5/242 |
| | | | | 431/12 |
| 2017/0108236 A1 * | 4/2017 | Guan | ................... | G05B 19/042 |

(Continued)

*Primary Examiner* — Hugh Maupin
(74) *Attorney, Agent, or Firm* — WPAT, PC

(57) ABSTRACT

There is provided an auto detection system including a thermal detection device and a host. The host controls an indication device to indicate a prompt message or detection results according to a slope variation of voltage values or 2D distribution of temperature values detected by the thermal detection device, wherein the voltage values include the detected voltage of a single pixel or the sum of detected voltages of multiple pixels of a thermal sensor.

12 Claims, 16 Drawing Sheets

(56) References Cited

U.S. PATENT DOCUMENTS

2018/0220768 A1* 8/2018 Boateng .................. A45D 2/001
2018/0242772 A1* 8/2018 Jenkins .................... H04B 5/73
2018/0253953 A1* 9/2018 Bucsa ....................... F24C 3/12
2019/0187636 A1* 6/2019 Fong .................. G05B 13/0265
2019/0212060 A1* 7/2019 Lintonen ................. F24C 7/082

* cited by examiner

AUTO DETECTION SYSTEM FOR COOKING ASSISTANCE AND HAIR DRYER WITH THERMAL DETECTION

RELATED APPLICATIONS

The present application is a continuation application of U.S. application Ser. No. 17/584,755, filed on Jan. 26, 2022, which is a continuation application of U.S. application Ser. No. 16/818,442, filed on Mar. 13, 2020, which claims the priority benefit of U.S. Provisional Application Ser. No. U.S. 62/887,740, filed on Aug. 16, 2019, the disclosures of which are hereby incorporated by reference herein in their entirety.

The U.S. application Ser. No. 16/818,442 is a continuation-in-part application of U.S. application Ser. No. 16/458,626, filed Jul. 1, 2019, which claims the priority benefit of U.S. Provisional Application Ser. Number U.S. 62/714,132, filed on Aug. 3, 2018, the disclosures of which are hereby incorporated by reference herein in their entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to an auto detection system and, more particularly, to an auto detection system that performs the electronic device control and message prompting based on thermal signals.

2. Description of the Related Art

In the image processing technology nowadays, it is able to perform various automatic controls according to images acquired by an image sensor, e.g., performing the ID recognition using images to accordingly control the corresponding electronic devices.

However, the privacy protection is gradually considered an important issue. Accordingly, in a public area, unless being used as a monitor device, the image sensor is no longer suitable to be used as an automatic control means. In addition, although a pyroelectric infrared (PIR) motion sensor has been broadly applied to the lamp control means as an automatic switch to save power by turning off the lamp in an area when there is no person in that area, the PIR motion sensor can lose its function when an object in the detected area thereof has no motion due to that the PIR motion sensor is essentially functioned to detect a moving object.

Accordingly, the present disclosure provides an auto detection system without using an image sensor or a PIR motion sensor and can be applied to the human detection in an elevator, the urine-wet detection, the stove detection, the hair temperature detection and the skin temperature detection.

SUMMARY

The present disclosure provides an auto detection system that identifies whether there is a person in an elevator cabin according to the slope of digital values, the fluctuation of digital values and the variation of temperatures outputted by a thermal sensor chip.

The present disclosure further provides an auto detection system that identifies a urine-wet condition of a diaper according to the slope of digital values outputted by a thermal sensor chip.

The present disclosure further provides an auto detection system that controls a display to show a 2D temperature distribution of multiple temperature values outputted by a thermal sensor chip as a reference for a user in cooking.

The present disclosure provides an auto detection system including a thermal detection device and a host. The thermal detection device has a field of view covering a pot on a stove, and includes a thermopile sensor array configured to output a thermal frame having multiple object temperatures. The host is configured to receive the multiple object temperatures, and control an indication device to remind a user to put ingredients in the pot upon identifying that at least one of the multiple object temperatures is larger than a heating threshold.

The present disclosure further provides an auto detection system including a thermal detection device and a host. The thermal detection device has a field of view covering ingredients, and includes a thermopile sensor array configured to output a thermal frame having multiple object temperatures. The host is configured to receive the multiple object temperatures, and control an indication device to remind a user to turn over the ingredients upon identifying that uniformity of the multiple object temperatures is lower than a uniformity threshold.

The present disclosure further provides a hair dryer including a thermal detection device and a host. The thermal detection device is configured to output an object temperature. The host is configured to identify a hair temperature according to the object temperature, and adjust at least one of a wind strength and a wind temperature upon the hair temperature exceeding a predetermined temperature threshold.

In the present disclosure, the thermal sensor includes a single thermopile sensor (i.e. outputting one voltage signal once) or a thermopile sensor array (i.e. outputting multiple voltage signals per frame). The thermal detection device includes an addition circuit used to perform the binning on multiple voltage signals outputted by multiple pixels of the thermal sensor. The voltage sum is then processed by the analog-digital-conversion so as to improve the signal-to-noise ratio and accuracy.

BRIEF DESCRIPTION OF THE DRAWINGS

Other objects, advantages, and novel features of the present disclosure will become more apparent from the following detailed description when taken in conjunction with the accompanying drawings.

Figures 3A, 3B, 3C, 3D:
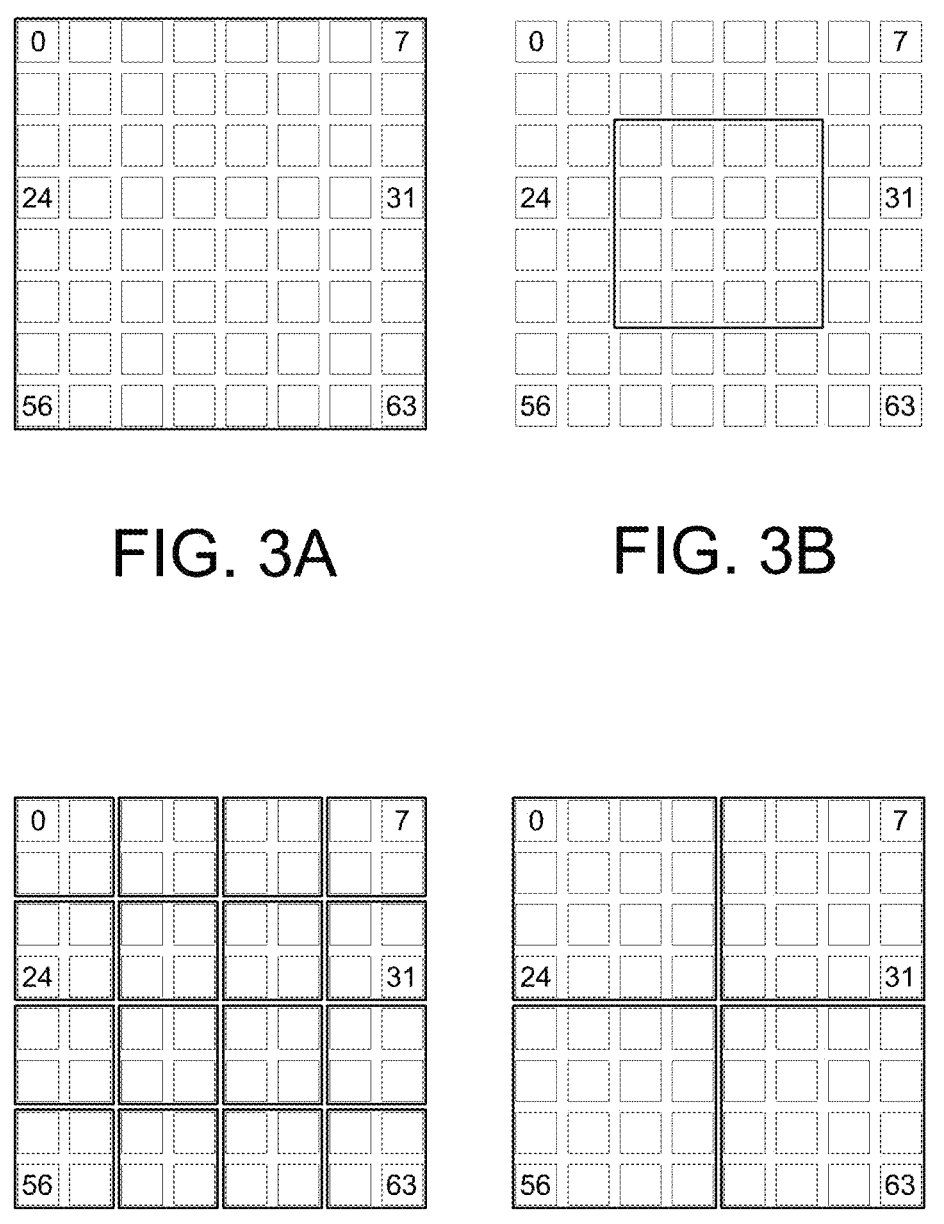

FIGS. 3A to 3D are schematic diagrams of the pixel binning according to some embodiments of the present disclosure.

DETAILED DESCRIPTION OF THE EMBODIMENT

It should be noted that, wherever possible, the same reference numbers will be used throughout the drawings to refer to the same or like parts.

The present disclosure provides an auto detection system that performs the electronic device control or the message prompting according to voltage signals or values outputted by a single thermopile sensor or a thermopile sensor array without using an image sensor or a pyroelectric infrared (PIR) motion sensor thereby solving the problems of privacy protection and steady object detection.

Figure 1:
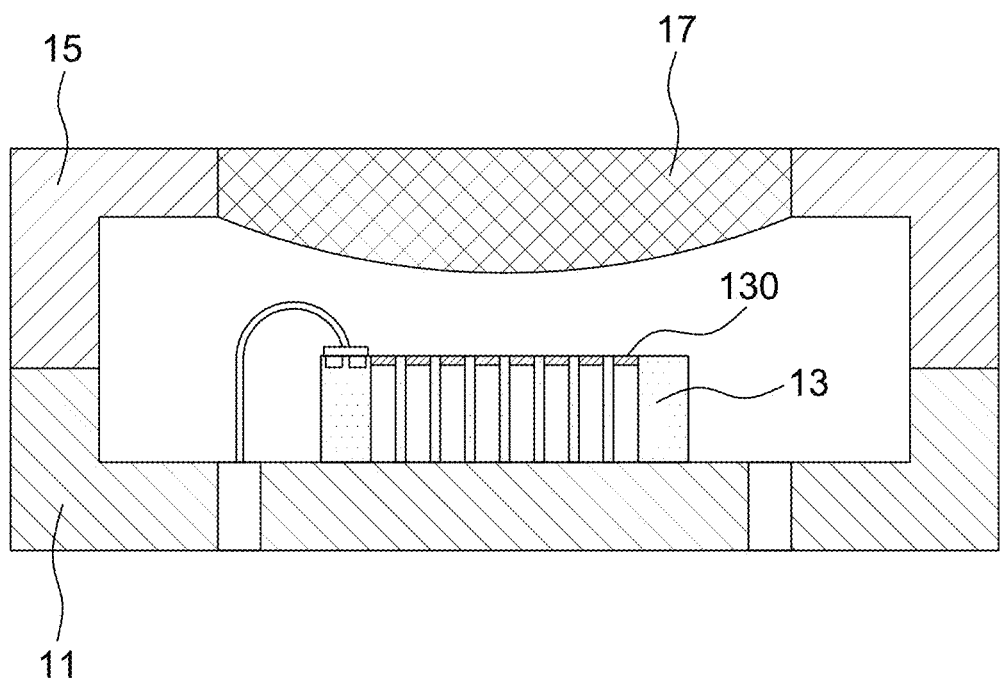
FIG. 1 is a cross-sectional view of a package of thermal sensor array according to one embodiment of the present disclosure.

Referring to FIG. 1, it is a cross-sectional view of a package of thermal sensor array 10 according to one embodiment of the present disclosure. The package of thermal sensor array 10 includes a circuit board 11, a sensor array integrated circuit 13, a package 15 and a filter 17. The sensor array integrated circuit 13 has multiple sensing elements (or called pixels) 130 arranged in a matrix, e.g., FIGS. 3A to 3D showing 8×8 sensing elements. The filter 17 is used to block light spectrum outside far infrared light. When the sensing elements 130 absorb far infrared light, a potential difference is formed at two terminals of the element to output a voltage signal as a detected signal. Each of the sensing elements 130 is, for example, a thermopile sensor, wherein the principle of a thermopile sensor that receives far infrared light to output a voltage signal is known to the art and thus details thereof are not described herein. Accordingly, the multiple sensing elements 130 of the package of thermal sensor array 10 output multiple voltage signals or voltage values to form a frame.

It should be mentioned that although FIG. 1 shows only one set of sensor array integrated circuit 13, the present disclosure is not limited thereto. In the case that a larger detection range is required, the package of thermal sensor array 10 includes multiple sets of sensor array integrated circuits 13 to output multiple sets of voltage signals or voltage values, and details thereof are referred to a U.S. Patent Application No. U.S. Ser. No. 16/294,873, file on Mar. 6, 2019 and entitled "FAR INFRARED SENSOR APPARATUS HAVING MULTIPLE SENSING ELEMENT ARRAYS INSIDE SINGLE PACKAGE", assigned to the same assignee of the present disclosure, and the full disclosure of which is incorporated herein by reference.

Figure 2:
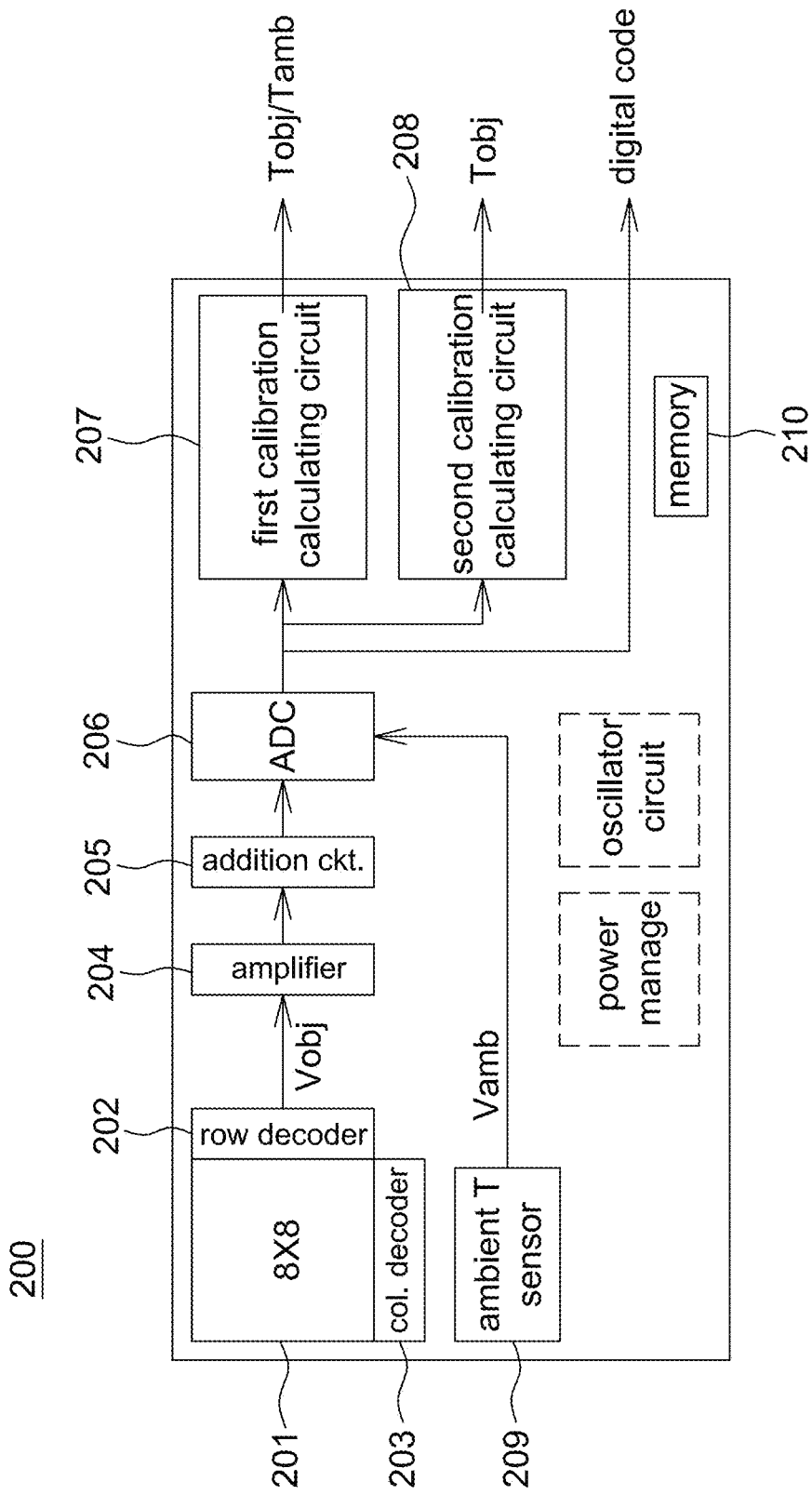
FIG. 2 is a schematic block diagram of a thermal detection device according to one embodiment of the present disclosure.

Referring to FIG. 2, it is a schematic block diagram of a thermal detection device 200 according to one embodiment of the present disclosure. The thermal detection device 200 is formed as, for example, a chip package that is encapsulated by a casing to form a device similar to a camera, but not limited to. The thermal detection device 200 includes a thermal sensor 201, a row decoder 202, a column decoder (shown as col. decoder) 203, an amplifier 204, an addition circuit (shown as addition ckt.) 205, an analog-to-digital converter (ADC) 206, a first calibration calculating circuit 207, a second calibration calculating circuit 208, and an ambient temperature sensor (shown as ambient T sensor) 209.

The thermal sensor 201 includes, for example, the package of thermal sensor array 10 mentioned above. According to control signals of the row decoder 202 and the column decoder 203, voltage signals or voltage values Vobj of every pixel are sequentially readout (by scanning and sampling procedure) from the thermal sensor 201, wherein the method of scanning a pixel array according to the control signals of a row decoder and a column decoder is known to the art and thus details thereof are not described herein.

In the present disclosure, the thermal sensor 201 is used to detect far infrared light generated from the object within a field of view thereof. The ambient temperature sensor 209 is selected from, for example, the temperature meter other than the far infrared sensor. The ambient temperature sensor 209 is used to detect ambient temperature surrounding the thermal detection device 200 and output voltage signals or voltage values Vamb to the ADC 206, wherein by using different types of temperature meters, the ambient temperature sensor 209 generates a current signal at first and then the current signal is converted to the voltage signal Vamb. The detection frequency of the thermal sensor 201 is arranged to be identical to or different from the detection frequency of the ambient temperature sensor 209.

The amplifier 204 is, for example, a programmable game amplifier (PGA) that is used to amplify the voltage signal or value Vobj outputted by the thermal sensor 201. It should be mentioned that although FIG. 2 shows only one amplifier 204, the present disclosure is not limited thereto. The thermal detection device 200 includes multiple amplifiers 204 respectively coupled to one pixel row for amplifying the voltages on the connected pixel row.

The addition circuit 205 is used to perform the binning or summation of values of multiple voltage signals generated by the thermopile sensor array, if being adopted, to achieve the purposes of improving the signal-to-noise (SNR) and increasing amplitude of the voltage signal to improve the resolution. In the present disclosure, a pixel number or pixel region that the addition circuit 205 performs the binning thereof is determined according to different applications. For example, in FIG. 3A, the addition circuit 205 performs the binning of voltage signals of all pixels (e.g., 8×8 pixel array being taken as an example herein) to obtain one voltage sum to be outputted to the ADC 206; in FIG. 3B, the addition circuit 205 performs the binning of voltage signals of a central 4×4 window and the voltage signals of other pixels outside the 4×4 window is maintained as they are, e.g., obtaining one voltage sum associated with the 4×4 window and 48 voltage signals associated with every single pixel to be outputted to the ADC 206; in FIG. 3C, the pixel array is divided into 16 regions and the addition circuit 205 performs the binning of 4 voltage signals at each region to obtain 16 voltage sums to be outputted to the ADC 206; and in FIG. 3D, the pixel array is divided into 4 regions and the addition circuit 205 performs the binning of 16 voltage signals at each region to obtain 4 voltage sums to be outputted to the ADC 206. It is appreciated that the binning shown in FIGS. 3A to 3D is only intended to illustrate but not to limit the present disclosure.

The ADC 206 is used to convert each voltage signal Vobj or each voltage sum from the addition circuit 205 to a digital code, each digital code has a digital value. The ADC 206 is further used to convert the voltage signal or voltage value Vamb into the digital signal. The ADC 206 may generate a number of digital values associated with Vobj different from a number of digital values associated with Vamb within the same time interval.

The first calibration calculating circuit 207 is used to convert the digital value associated with the voltage signals without the binning to the temperature signal, e.g., the digital value associated with one voltage signal Vobj or Vamb corresponding to one temperature value or the digital values associated with multiple voltage signals Vobj or Vamb corresponding to one identical temperature value (in the case that the resolution of digital value being larger than the resolution of temperature value). The thermal detection device 200 preferably further has a memory 210 used to previously record the corresponding relationship or algorithm between the digital value (or digital code) and the temperature value such that when the digital value of one voltage signal Vobj or Vamb is received from the ADC 206, a corresponding temperature value Tobj or Tamb is calculated by the first calibration calculating circuit 207.

The second calibration calculating circuit 208 is used to convert the digital value associated with the voltage sum obtained by the binning (e.g., adding the values of multiple voltage signals) to the temperature signal, e.g., the digital value associated with one voltage sum corresponding to one temperature value or the digital values associated with multiple voltage sums corresponding to one identical temperature value. As the binned voltage sum and the voltage signal without the binning have different conditions, the second calibration calculating circuit 208 is further provided to perform the conversion from digital values to temperature values. The memory 210 preferably further records the corresponding relationship or algorithm between the digital value (or digital code) of voltage sum and the object temperature Tobj such that when the digital value of one voltage sum is received from the ADC 206, a corresponding temperature value is calculated by the second calibration calculating circuit 208. In one non-limiting aspect, the second calibration calculating circuit 208 outputs only the object temperature Tobj without outputting the ambient temperature Tamb.

The thermal detection device 200 includes, for example, a multiplexer or a switching element used to transfer the digital value of voltage signals to the first calibration calculating circuit 207, and transfer the digital value of voltage sums to the second calibration calculating circuit 208. In one non-limiting aspect, the thermal detection device 200 includes two ADC used to convert the digital signal of Vobj and Vamb, respectively.

Accordingly, the thermal detection device 200 outputs digital values (associated with Vobj only), object temperatures Tobj and ambient temperatures Tamb at predetermined frequencies identical to or different from one another, wherein the predetermined frequency is, for example, 1 to 3 times per second according to different applications. In the present disclosure, the digital value outputted by the thermal detection device 200 includes the detection result of the thermal sensor 201 to be used later (described below by an example) without the detection result of the ambient temperature sensor 209. The detection result of the ambient temperature sensor 209 is outputted as ambient temperature Tamb, which is converted by the first calibration calculating circuit 207.

The thermal detection device 200 of the present disclosure further includes other circuits such as a power management circuit and an oscillation circuit, and details thereof are known to the art and thus not described herein. Different applications of the thermal detection device 200 are described hereinafter.

Figure 4:
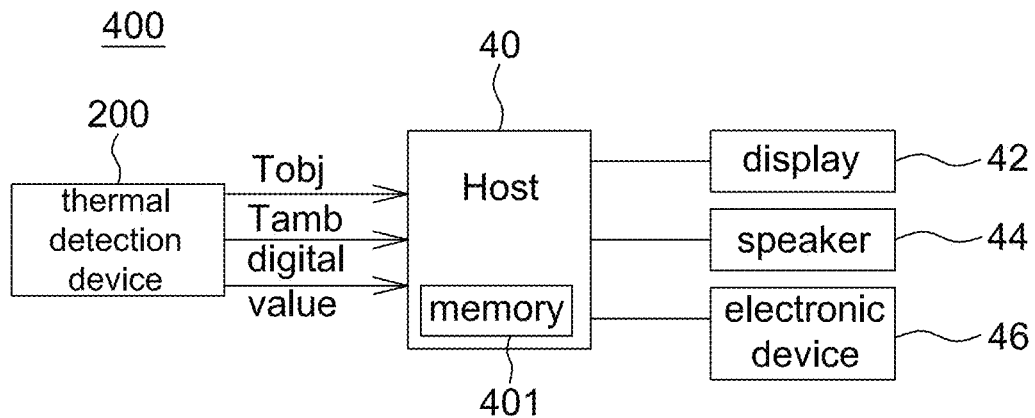
FIG. 4 is a schematic block diagram of an auto detection system according to one embodiment of the present disclosure.

Referring to FIG. 4, it is a schematic block diagram of an auto detection system 400 according to one embodiment of the present disclosure. The auto detection system 400 includes a thermal detection device 200 and a host 40 coupled to each other in a wired or wireless manner to communicate therebetween. The thermal detection device 200 may use that shown in FIG. 2, and is arranged, for example, on an electronic device 46 to output digital values, object temperatures Tobj and ambient temperatures Tamb according to the detection result thereof. The host 4 is a computer device equipped with a central processing unit (CPU) and/or a microcontroller unit (MCU) such as, for example, a desktop computer, a notebook computer, a tablet computer, a smart phone, a central server or the like. The host 4 is directly integrated with a display device 42 and/or a speaker 44, or coupled with the display device 42 and/or the speaker 44 in a wired or wireless manner. In this way, the host 4 receives the digital values, object temperatures Tobj and ambient temperatures Tamb from the thermal detection device 200 to control the display device 42, the speaker 42 and/or the electronic device 46, which is, for example, a device that the thermal detection device 200 is applied to.

Figure 5:
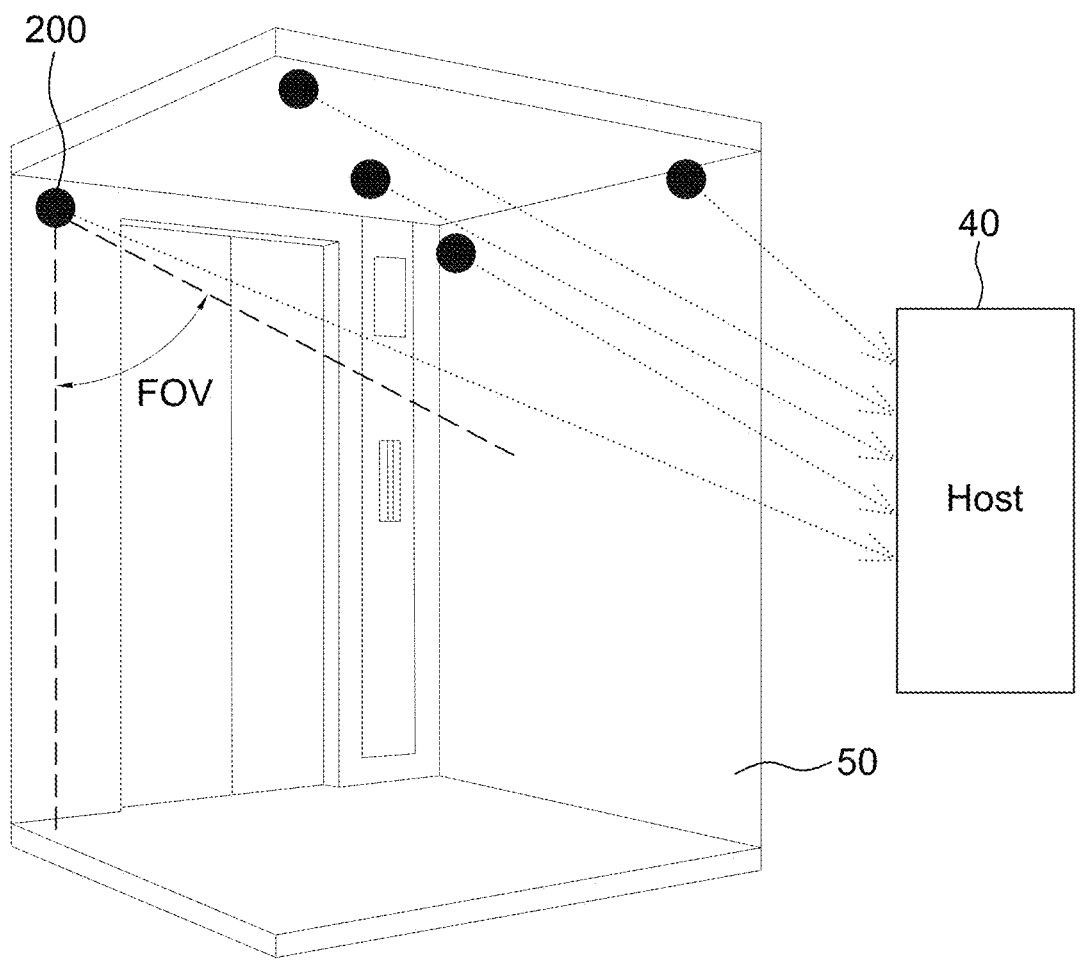
FIG. 5 is a schematic diagram of an auto detection system according to a first embodiment of the present disclosure.

Referring to FIG. 5, it is a schematic diagram of the application of an auto detection system 400 according to a first embodiment of the present disclosure. In the first embodiment, at least one thermal detection device 200 (e.g., 5 thermal detection devices being shown in FIG. 5 at different positions) is arranged at a ceiling or close to the ceiling of an elevator cabin 50, and each thermal detection device 200 has its own field of view FOV (for simplification only one being shown). In the first embodiment, as the auto detection system 400 is used to detect whether the elevator cabin 50 has a person therein or not, the FOV of the thermal detection device 200 preferably covers only an inside area of the elevator cabin 50 without covering the area outside an entrance (i.e. outside the elevator) of the elevator cabin 50. In the present disclosure, the thermal detection device 200 is preferably arranged at two sides above the entrance or at a central area of the ceiling of the elevator cabin 50. Preferably, the field of view FOV of the thermal detection device 200 does not cover the entrance of the elevator cabin 50 to reduce the influence from the opening and closing of the cabin door.

As mentioned above, each thermal detection device 200 outputs digital values, object temperatures Tobj and ambient temperatures Tamb respectively at a predetermined frequency to the host 40. The host 40 is located, for example, at a central control room, a guardroom or held by a staff outside the elevator cabin 50 for the staff to monitor whether there is a person in the elevator cabin 50 or not via the display device 42, the speaker 44, lamps or other indicating means. In the present disclosure, the display device 42 does not show the inner image of the elevator cabin 50, and the indication of whether there is a person in the elevator cabin 50 or not is shown by words or graphs on the display device 42 for the privacy protection.

In the first embodiment, the thermal detection device 200 includes a single thermopile sensor or a thermopile sensor array. For the thermopile sensor array case, the thermal detection device 200 has a pixel array (e.g., 201) for outputting multiple voltage signals Vobj (or called a frame) every sampling period. As mentioned above, the addition circuit 205 is used to sum up a part or all of the multiple voltage signals Vobj (more specifically the amplified voltage signals) to generate a voltage sum(s). The ADC 206 is used to convert the voltage signal Vobj and the voltage sum into the digital value. The first calibration calculating circuit 207 is used to convert and output the object temperature Tobj according to the digital value associated with the voltage signal Vobj. The second calibration calculating circuit 208 is used to convert and output the object temperature Tobj according to the digital value associated with the voltage sum. It is appreciated that the resolution of the digital value is determined by the resolution of the ADC 206, e.g., 0-255, but not limited to.

After receiving the detection result from the thermal detection device 200, the host 40 calculates a slope between two digital values, a fluctuation degree of multiple digital values and a temperature variation of the object temperatures Tobj corresponding to each thermal detection device 200, and then identifies whether the elevator cabin 50 has a person therein or not according to the calculated slope, fluctuation degree and temperature variation. The host 40 performs the identification according to the outputted parameter of each thermal detection device 200, respectively, to obtain multiple identification results. The method of identifying the existence of a person according to one thermal detection device 200 is illustrated hereinafter.

Figure 6:
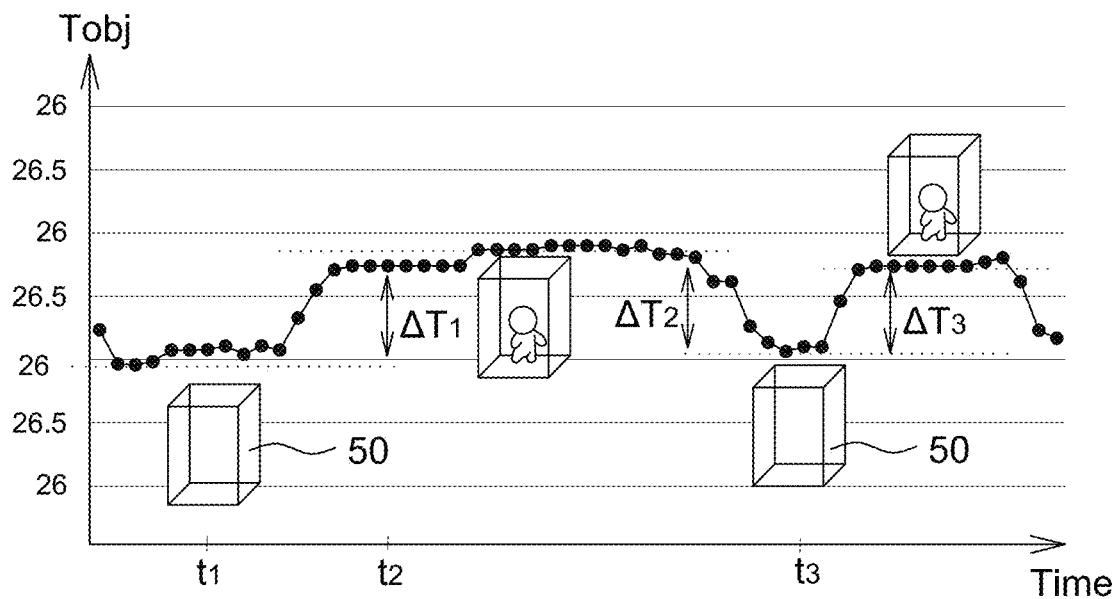
FIG. 6 is a schematic diagram of the temperature variation of an auto detection system according to a first embodiment of the present disclosure.

Referring to FIG. 6, it is a schematic diagram of a variation of the object temperature Tobj when there is a person and no person in an elevator cabin 50. It is seen from FIG. 6 that when a person enters or leaves the elevator cabin 50, the object temperature Tobj changes to have a temperature variation, e.g., $\Delta T1$, $\Delta T2$ and $\Delta T3$, wherein values of $\Delta T1$, $\Delta T2$ and $\Delta T3$ are identical to or different from each other according to the human height, human body temperature, ambient temperature or other environmental conditions. When the temperature variation (increment or decrement) exceeds a temperature threshold, it is able to identify a person in/out. In the present disclosure, the temperature variation is, for example, a difference between two adjacent (in timeline) object temperatures Tobj outputted by the thermal detection device 200, two object temperatures Tobj separated by a predetermined time interval, or a difference between a current object temperature (e.g., at time t2) outputted by the thermal detection device 200 and a recorded object temperature (e.g., at time t1) stored when the elevator cabin 50 has no person therein.

In other words, the host 40 preferably includes a memory 401 used to record an object temperature Tobj when there is no person in the elevator cabin 50 (e.g., at time t1) as a reference temperature to avoid error caused by the ambient temperature variation. The host 40 updates the reference temperature every predetermined time when the elevator cabin 50 continuously has no person therein, or the host 40 updates the reference temperature (e.g., at time t3) after a person(s) enters and leaves the elevator cabin 50 to increase the identification accuracy.

However, it is noticed that there are many reasons that can influence the object temperature Tobj. Accordingly, the present embodiment further uses other detected parameters in addition to the object temperature Tobj to identify whether the elevator cabin 50 has a person therein or not.

Figure 7A:
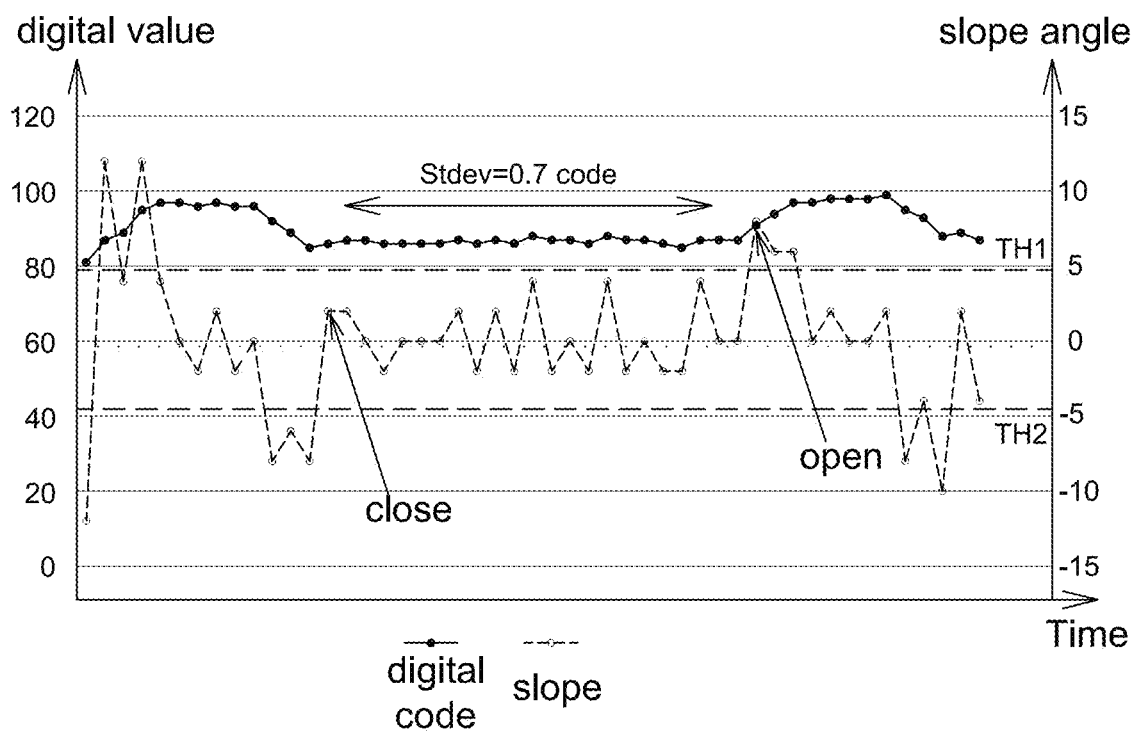
FIG. 7A is a schematic diagram of the digital value variation and the slope variation of an auto detection system according to a first embodiment of the present disclosure, wherein no person is in an elevator cabin.

Referring to FIG. 7A, it is a schematic diagram of the digital value (associated with the voltage signal Vobj or voltage sum) fluctuation (indicated by solid line) and the slope variation (indicated by dotted line) when there is no person in an elevator cabin 50. The reason of using the digital value to perform the identification is that the resolution of digital value can be set to be larger than the resolution of temperature value to obtain more accurate identification result.

In the first embodiment, the host 40 calculates a slope between two digital values, wherein said two digital values are two adjacent (in timeline) digital values outputted by the thermal detection device 200. As mentioned above, the thermal detection device 200 is set to output 1 to 3 digital values per second. When the slope between two digital values exceeds a slope threshold value or a slope threshold range, e.g., TH1 and TH2 in FIG. 7A, it means that the door of the elevator cabin 50 is opened and a person might enter or leave the elevator cabin 50. It is seen from FIG. 7A that when the door of the elevator cabin 50 opens and closes, the slope have an obvious change (e.g., exceeding a threshold).

In addition, to increase the identification accuracy, the host 40 further identifies whether a fluctuation degree of multiple digital values exceeds a code variation threshold. For example, the fluctuation degree is preferably a standard deviation, shown as Stdev in FIG. 7A, of multiple digital values within a predetermined time interval after the slope between the two digital values exceeds the slope threshold. In one aspect, Stdev is a standard deviation of multiple digital values within the predetermined time interval after the slope changes back to be within a predetermined threshold range (e.g., between TH1 and TH2). It is seen from FIG. 7A that the slope exceeds the predetermined threshold range when the cabin door opens and then goes back to be within the predetermined threshold range after the cabin door closes.

Figure 7B:
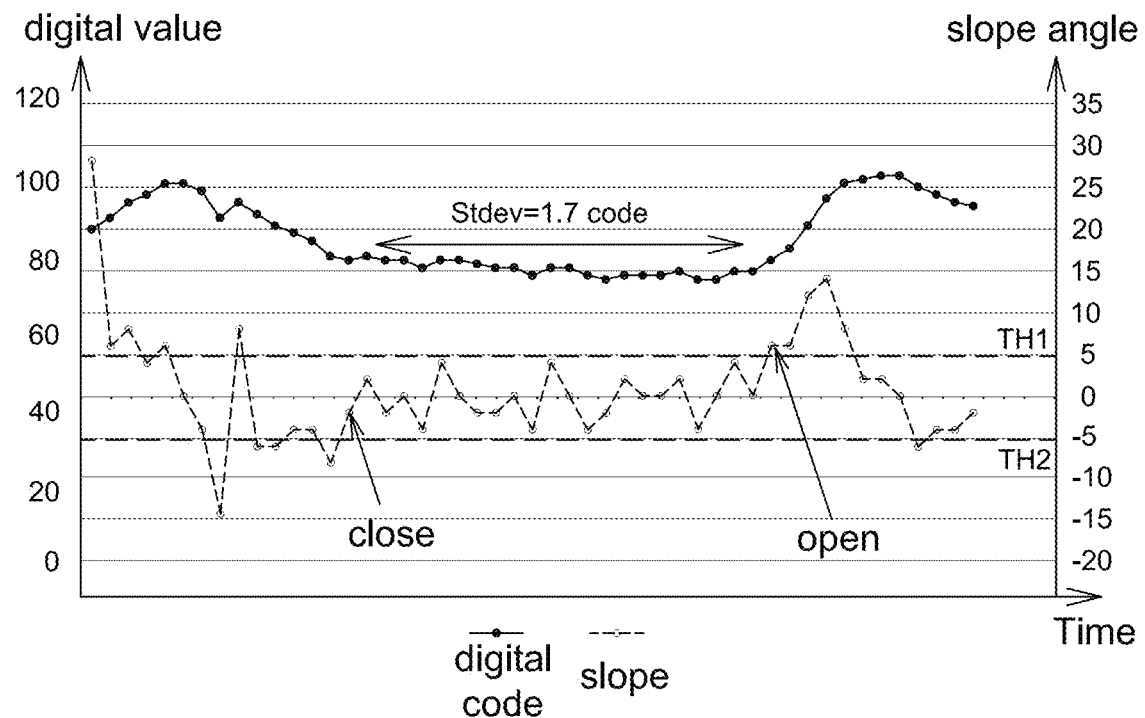
FIG. 7B is another schematic diagram of the digital value variation and the slope variation of an auto detection system according to a first embodiment of the present disclosure, wherein at least one person is in an elevator cabin

Referring to FIG. 7B together, it is a schematic diagram of the digital value fluctuation (indicated by solid line) and the slope variation (indicated by dotted line) when there is a person in an elevator cabin 50. It is seen from FIGS. 7A and 7B that the slope between two digital values exceeds the predetermined threshold range (e.g., between TH1 and TH2) when the door of the elevator cabin 50 opens (no matter whether there is a person entering or leaving) and then goes back to be within the predetermined threshold range after the cabin door closes. Accordingly, it is not easy to identify the entering/leaving person only according to the slope variation. But it is seen from FIGS. 7A and 7B that when there is a person in the elevator cabin 50, the fluctuation degree Stdev of multiple digital values (e.g., FIG. 7B) within a predetermined time interval (e.g., 3-10 seconds, but not limited to) is larger than the fluctuation degree Stdev when there is nobody in the elevator cabin 50 (e.g., FIG. 7A). The reason is considered that the person in the elevator cabin 50 causes a larger disturbance to the temperature. Accordingly, the first embodiment performs the human identification using 3 parameters to effectively improve the identification accuracy. In the case of FIGS. 7A and 7B, a code variation threshold is set, for example, as 1.0 code.

It should be mentioned that the fluctuation degree is not limited to be calculated by using the standard deviation, and may be obtained by calculating other parameters that can be used to indicate the fluctuation of the digital values.

Figure 8:
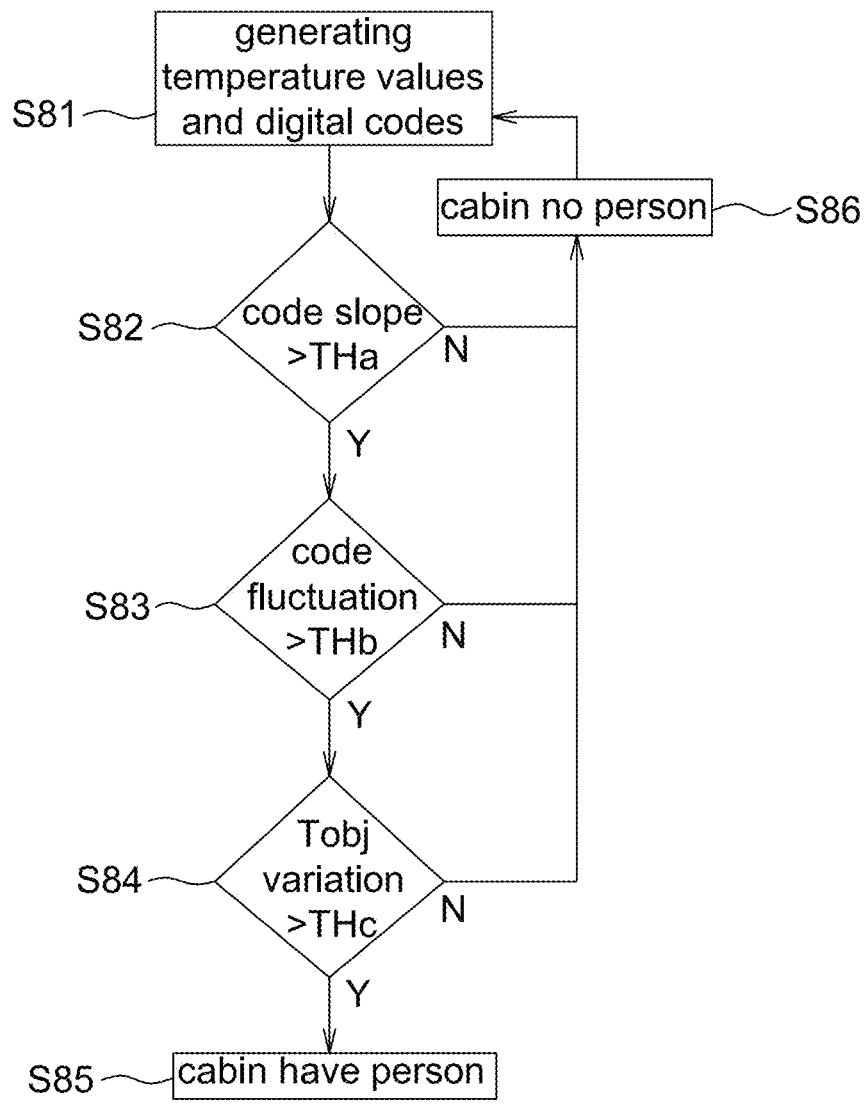
FIG. 8 is an operational flow chart of an auto detection system according to a first embodiment of the present disclosure.

Referring to FIG. 8, it is an operational flow chart of an auto detection system 400 according to a first embodiment of the present disclosure, including the steps of: generating temperature values and digital codes (Step S81); comparing a code slope with a slope threshold THa (Step S82); comparing a code fluctuation with a code variation threshold THb (Step S83); comparing a temperature variation with a temperature threshold THc (Step S84); and identifying whether an elevator cabin has a person or not (Steps S85-S86), wherein THa, THb and THc indicate a single value or a value range, respectively.

Referring to FIGS. 4 to 8 together, the thermal detection device 200 firstly sends the detected digital values (i.e. values of digital codes) and object temperatures Tobj to the host 40, Step S81.

In this embodiment, the host 40 identifies the elevator cabin 50 having a person therein only when the slope between two digital values exceeds a slope threshold or threshold range (referring to FIGS. 7A and 7B), the fluctuation degree Stdev of multiple digital values exceeds a code variation threshold or threshold range (referring to FIGS. 7A and 7B), and the temperature variation exceeds a temperature threshold or threshold range (referring to FIG. 6), Step S82-S85. When any one of the Steps S82-S84 is not true, the elevator cabin 50 is identified having no person therein, Step S86.

No matter what is the identification result, the host 40 indicates whether the elevator cabin 50 has a person or not via a coupled indication device (e.g., display device 42, speaker 44 and/or lamp), or via a coupled mobile device (e.g., smart phone or smart watch).

In this embodiment, the host 40 further detects whether the temperature in the elevator cabin 50 is normal or abnormal according to the ambient temperature Tamb. If the ambient temperature Tamb is too high or too low, a warning message is indicated via the indication device or the mobile device. In addition, the host 40 further adjusts the slope threshold, the code variation threshold and/or the temperature threshold according to the ambient temperature Tamb to eliminate the interference brought by the environment change.

In one non-limiting embodiment, if the auto detection system 400 includes more than one thermal detection device 200. When identifying that the elevator cabin 50 has a person therein according to one of the multiple thermal detection devices 200, the host 40 identifies that the elevator cabin 50 is occupied by a person(s). The host 40 is not necessary to identify the elevator cabin 50 being occupied after all thermal detection devices 200 are identified to have a person therein.

In one non-limiting embodiment, if the auto detection system 400 includes a thermopile sensor array. When identifying that the elevator cabin 50 has a person therein according to a predetermined number of pixels or pixel regions (e.g., sub-regions shown in FIGS. 3C-3D) of a pixel array of the thermopile sensor array, the host 40 identifies that the elevator cabin 50 is occupied by a person(s), wherein the predetermined number is smaller than a pixel number or a region number of the pixel array. The host 40 is not necessary to identify the elevator cabin 50 being occupied after all pixels or pixel regions are identified to have a person therein. The method of identifying a person based on each pixel or pixel region is referred to FIG. 8.

In another non-limiting aspect, one pixel of the thermopile sensor array is turned on at first, and when the object temperature Tobj detected by the one pixel exceeds a temperature threshold, the rest pixels are then turned on.

In the first embodiment, after the elevator cabin 50 is identified to have a person in Step S85, the host 40 continuously identifies whether the person leaves or not according the digital values and object temperatures Tobj sent from the thermal detection device 200 based on the Steps S82 and S83. For example in FIG. 7B, when the cabin door is opened and a person leaves the elevator cabin 50, the curves in FIG. 7B change to FIG. 7A to cause the fluctuation degree Stdev to be smaller than THb. In this way, the host 40 confirms that the elevator cabin 50 has no person therein. The host 40 further confirms that a person leaves the elevator cabin 50 according to FIG. 6. As mentioned above, the host 40 updates the reference temperature of the elevator cabin 50 (as shown in FIG. 6 temperatures at times t1 and t3 having different values) to be used in the next round of identification.

In other aspects, the auto detection system 400 further includes at least one thermal detection device 200 arranged outside the elevator cabin 50 to monitor the elevator shaft to identify whether there is a person in the elevator shaft.

Figure 9:
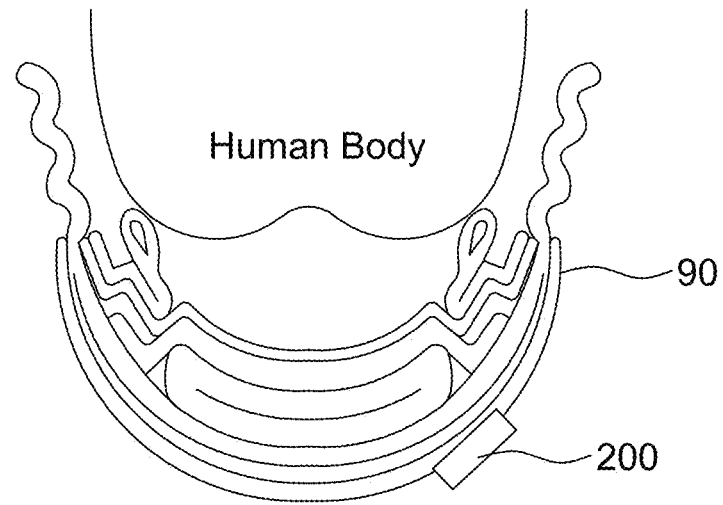
FIG. 9 is a schematic diagram of an auto detection system according to a second embodiment of the present disclosure.

Referring to FIG. 9, it is a schematic diagram of an auto detection system 400 according to a second embodiment of the present disclosure. In this embodiment, the auto detection system 400 is applied to the urine-wet detection of a diaper. Compared with the conventional urine-wet detection by using a moisture sensor, the casing of the auto detection system 400 of the present disclosure does not have an opening to allow the moisture to come in such that an enclosed structure is formed without being influenced by the sweat moisture. The thermal detection device 200 is arranged at different positions to be suitable for male products or female products.

The auto detection system 400 of this embodiment also includes a thermal detection device 200 and a host 40 coupled to each other. As shown in FIG. 9, the thermal detection device 200 is arranged on the diaper 90 and used to output digital values at a predetermined frequency. In this embodiment, the auto detection system 400 outputs or does not output object temperatures Tobj according to different applications. The thermal detection device 200 also includes a single thermopile sensor or a thermopile sensor array without particular limitations. When the thermal detection device 200 adopts the thermopile sensor array, the thermal detection device 200 also performs the aforementioned binning procedure on a part of or all multiple voltage signals outputted by the thermal sensor 201 thereof.

The host 40 communicates with the thermal detection device 200 in a wired or wireless manner. Examples of the thermal detection device 200 and the host 40 have been described above, and thus only the operating method thereof are described hereinafter.

Figure 10:
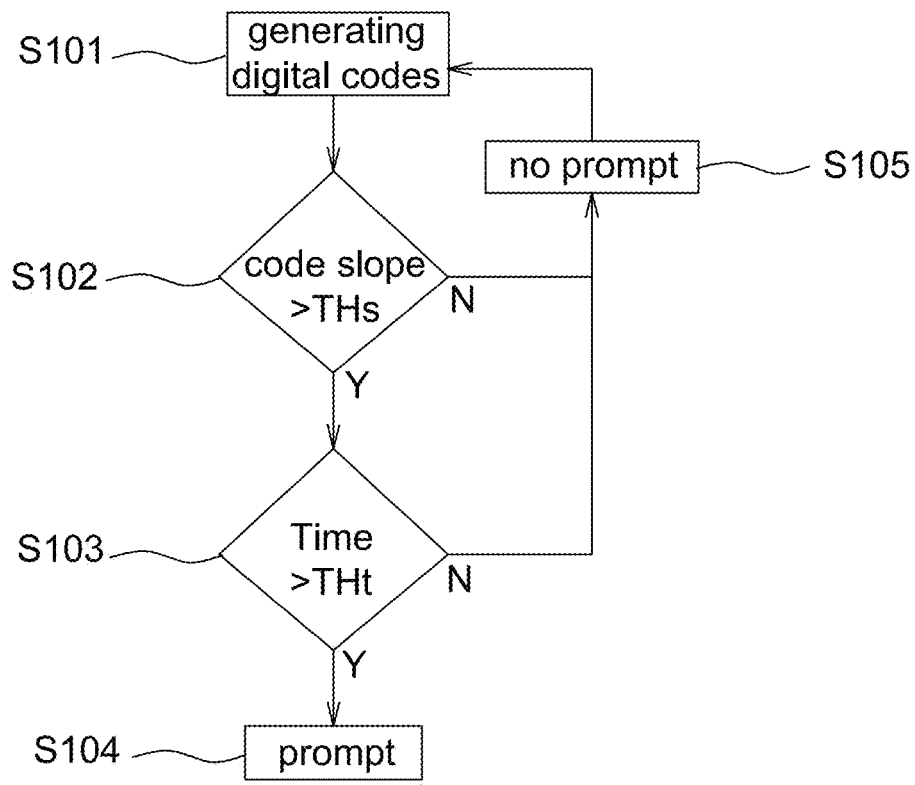
FIG. 10 is an operational flow chart of an auto detection system according to a second embodiment of the present disclosure.

Referring to FIG. 10, it is an operational flow chart of an auto detection system 400 according to a second embodiment of the present disclosure, including the steps of: generating digital codes (Step S101); comparing a code slope with a slope threshold THs (Step S102); conforming whether a continuous time exceeds a time threshold THt (Step S103); and determining whether to give a warning or not (Steps S104-S105).

Step S101: The thermal detection device 200 disposed in the diaper 90 has, for example, a press button or a switch. When the diaper 90 is worn on a human body, the thermal detection device 200 is activated to operate by using the press button or the switch; or the thermal detection device 200 starts to operate after a connection between the thermal detection device 200 and the host 40 is accomplished. Then, the host 40 receives the digital values generated by the ADC 206 of the thermal detection device 200. In this embodiment, the digital values are associated with the voltage signal or the voltage sum depending on the type of the thermopile sensor being used. As it is possible to set the digital values to have higher resolution than the object temperatures Tobj, the digital value is selected for the urine-wet detection. According to different implementation, the host 40 further receives object temperatures Tobj from the thermal detection device 200 for double check or other identifications.

Step S102: After receiving the digital values sequentially, the host 40 (e.g., the processor thereof) calculates a slope between two digital values to be compared with a slope threshold THs. In one aspect, a time interval for calculating the slope between the two digital values is between, for example, 0.5 and 1.5 seconds i.e., a period of outputting the digital values is between 0.5 and 1.5 seconds. Preferably, when a different time interval is selected, the slope threshold THs is also changed. When the slope is larger than the slope threshold THs, the Step S103 is entered; otherwise the Step S105 is entered and no warning is provided.

In another aspect, the host 40 identifies whether the calculated slope is between a predetermined range, e.g., larger than the slope threshold THs and smaller than another slope threshold. The another slope threshold is for preventing error due to the slope variation caused by other reasons since the urine temperature is generally between a predetermined range.

Step S103: When identifying that the slope between two digital values is larger than a slope threshold THs or within a predetermined range, the host 40 then identifies whether the slopes between multiple sets of two digital values within a predetermined time interval (e.g., 5-7 seconds) are continuously larger than the slope threshold THs or within the predetermined range. When the calculated multiple slopes are larger than the slope threshold THs or within the predetermined range longer than the time interval THt, the Step S104 is entered; otherwise the Step S105 is entered and no warning is provided. In this embodiment, the urine-wet is confirmed only when multiple slopes are larger than the slope threshold THs or within the predetermined range for a predetermined time interval so as to avoid error due to the sensor falling off or diaper being taken off.

In another aspect, the predetermined ranges of the slope in Steps S102 and S103 are different. For example, in Step S103 the predetermined range is set as $THl1<slope<Thu1$, and in Step S103 the predetermined range is set as $THl2<slope<Thu2$, wherein $Thu1>Thu2$ and $THl1<THl2$, but not limited thereto.

Step S104: The host 40 generates a prompt signal to the indication device, e.g., the display device 42 and/or the speaker 44, or to a mobile device, e.g., a smart phone, to indicate a prompt message, e.g., changing a new diaper.

In some aspects, the thermal detection device 200 further outputs object temperatures Tobj or ambient temperatures Tamb to the host 40. The host 40 generates a warning signal when the object temperatures Tobj or the ambient temperatures Tamb exceed a predetermined range. For example, when the object temperatures Tobj or the ambient temperatures Tamb are too high, e.g., much higher than the urine temperature (e.g., Tobj or Tamb=40 to 45 degrees), the host 40 informs the indication device or the mobile device, using the warning signal, to generate a warning message such as images or sounds.

In addition, the host 40 of the second embodiment further double checks the urine-wet condition in conjunction with the fluctuation, difference, slope, waveform or the standard deviation of the object temperatures Tobj and/or the digital values within a predetermined time interval.

In addition, the host 40 of the second embodiment further identifies the wearing state of the diaper 90 according to whether the object temperature Tobj and/or the digital value is within a predetermined operation range.

Figure 11:
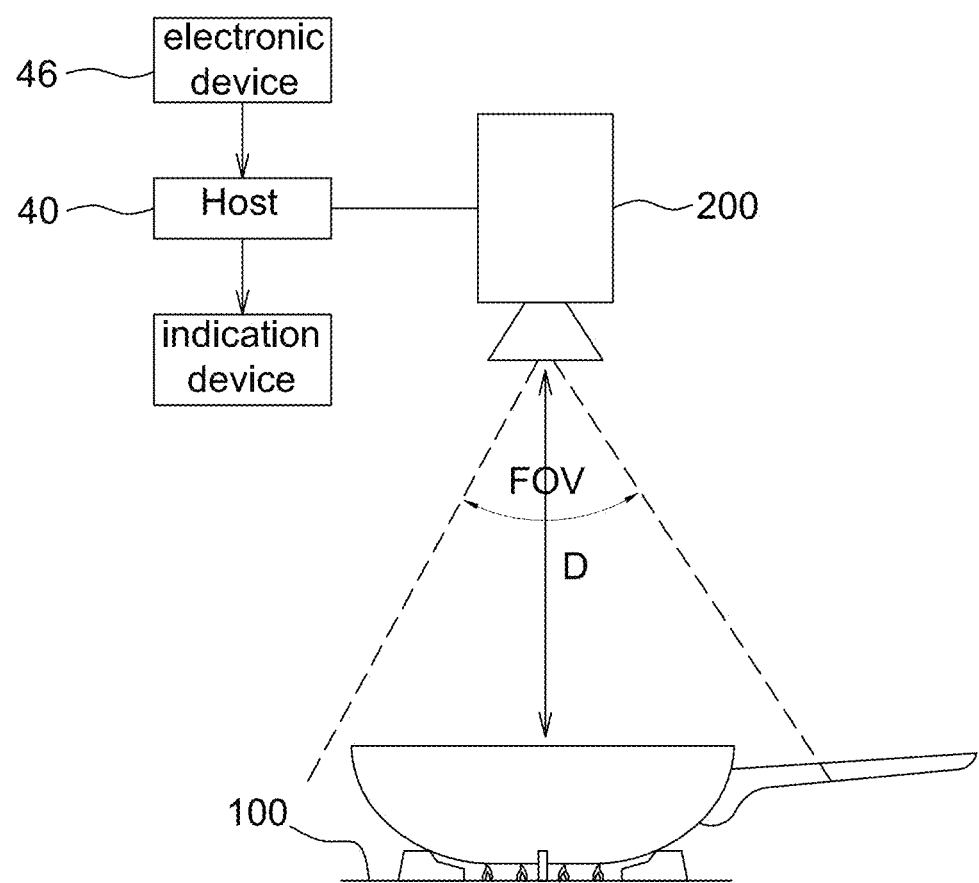
FIG. 11 is a schematic diagram of an auto detection system according to a third embodiment of the present disclosure.

Referring to FIG. 11, it is a schematic diagram of an auto detection system 400 according to a third embodiment of the present disclosure. In this embodiment, the auto detection system 400 is applied to the stove detection in the kitchen, e.g., overheating, forgetting to turn off the stove, cooking assistance or the like. The auto detection system 400 includes at least one thermal detection device 200. A number of the thermal detection device 200 is determined according to the area to be detected without particular limitations.

The auto detection system 400 of this embodiment also includes a thermal detection device 200 and a host 40 coupled to each other. The thermal detection device 200 has a field of view FOV covering the stove 100 and outputs object temperatures Tobj at a predetermined frequency. It should be mentioned that although FIG. 11 shows that the thermal detection device 200 is arranged right above the stove 100, the present disclosure is not limited thereto. The thermal detection device 200 may be arranged at any suitable angle as long as the FOV thereof covers the stove 100, and the stove 100 is not limited to heat a pot.

The host 40 is coupled to the thermal detection device 200 in a wired or wireless manner to receive object temperatures Tobj for controlling an extraction fan, the stove fire, a display device and/or other equipment in the kitchen according to the object temperatures Tobj. The host 40 is wired or wirelessly coupled to the electronic device 46 or integrated therein.

In one non-limiting aspect, the host 40 and the thermal detection device 200 are both integrated in the extraction fan. The host 40 is used to turn on the extraction fan when identifying that the object temperature Tobj exceeds a room temperature threshold (indicating the stove being turned on). The host 40 is further used to automatically adjust the wind strength of the extraction fan according to a variation of the object temperature Tobj (indicating the stove changing). In the case that the host 40 are separated from the extraction fan, the host 400 still automatically controls the extraction fan in a wired or wireless manner or informs a user to turn on the extraction fan via a display device 42.

In another non-limiting aspect, the host 40 is further used to control the indication device (e.g., including the display device 42 and/or speaker 44) to show a warning message when identifying that the object temperature Tobj exceeds a high temperature threshold, wherein the indication device is embedded in the host 40 or the electronic device 46, or separated therefrom.

Figure 12A:
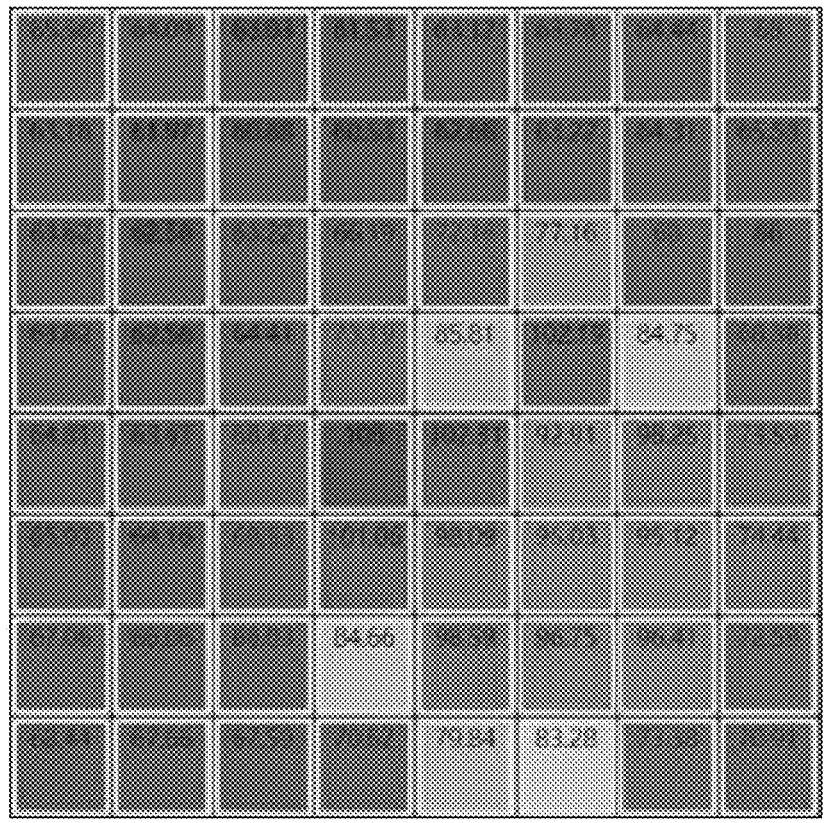
FIGS. 12A and 12B are schematic diagrams of the 2D temperature distribution of an auto detection system according to a third embodiment of the present disclosure.
Figure 12B:
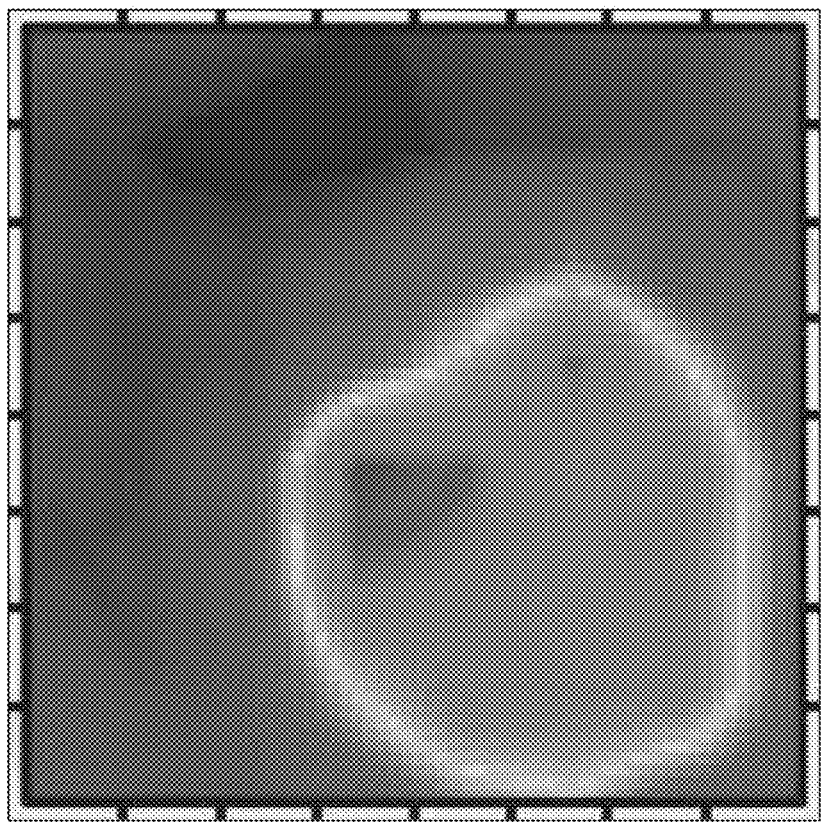

In another non-limiting aspect, the host 40 turns off the stove when identifying that the FOV of the thermal detection device 200 does not have any movement of a human body for a predetermined time interval. In this aspect, the thermal detection device 200 preferably includes a thermopile sensor array for outputting a thermal frame containing multiple object temperatures Tobj (e.g., each pixel outputting one object temperature) at a predetermined frequency. The host 40 controls the display device according to the thermal frame to show the multiple object temperatures by a 2-dimensional (2D) image, as shown in FIGS. 12A and 12B for example. In FIG. 12A, each rectangular region indicates a detected value of one pixel or one pixel region. For example, the display device 42 directly shows the object temperatures Tobj (e.g., values in every rectangular region in FIG. 12A) at the corresponding regions. In other aspects, the display device 42 shows high/low temperatures by different colors or brightness as FIG. 12B without showing values of the object temperatures Tobj.

In this way, the host 40 performs various identifications and gives a corresponding prompt message according to the thermal frame or the 2D image. For example, if the thermal frame or the 2D image does not contain the movement of a heating object (e.g., including a human body or heated shovel), it is identified that the FOV of the thermal detection device 20 does not have movement of a human body.

For example, in preheating a pot, when identifying that at least one of the multiple object temperatures Tobj of the thermal frame is larger than or equal to a heating threshold, the host 40 controls the indication device to indicate the message of a target temperature being reached so as to remind the user to put ingredients in the pot. For example, when identifying that the uniformity of the multiple object temperatures Tobj of the thermal frame is lower than a uniformity threshold, the host 40 controls the indication device to show the message of nonuniform temperature to remind the user to turn over the ingredients.

If the display device 42 shows a current temperature distribution real-timely as FIGS. 12A and 12B, the user can know the current operation temperature through the display device 42.

In one non-limiting aspect, the thermal detection device 200 further outputs ambient temperatures Tamb to the host 40. When identifying that the ambient temperatures Tamb exceed a predetermined temperature threshold, the host 40 controls the cooling equipment such as a cooling fan or air conditioner to decrease the temperature in the kitchen.

It is appreciated that the numbers, including temperatures, digital values, pixel numbers and thresholds, mentioned in the above embodiments are only intended to illustrate but not to limit the present disclosure. Although the above embodiments are described in the way that the host 40 informs only the display device, a speaker and/or a mobile device as examples, the present disclosure is not limited thereto. In other aspects, the host 40 informs other electronic devices in a smart home according to the calculated and identified results.

For example, the thermal detection device 200 of the present disclosure is arranged on a hair dryer for detecting the hair temperature during operation to accordingly adjust the wind strength and/or the wind temperature, e.g., by adjusting the current flowing through the heating wire of the hair dryer. When the hair temperature (e.g., identified by the host 40 according to the object temperature Tobj) exceeds a predetermined temperature threshold, the wind strength and/or the wind temperature is decreased to prevent the hair from being damaged. On the contrary, the wind strength and/or the wind temperature is increased.

For example, the thermal detection device 200 of the present disclosure is arranged on an electric radiator for detecting the skin temperature during operation to accordingly adjust the radiation temperature and/or the wind temperature, e.g., by adjusting the current flowing through the heating wire of the electric radiator. When the skin temperature (e.g., identified by the host 40 according to the object temperature Tobj) exceeds a predetermined temperature threshold, the radiation temperature and/or the wind temperature is decreased to improve the user experience. On the contrary, the radiation temperature and/or the wind temperature is increased.

In one aspect, the thermal detection device 200 of the present disclosure is used as an optical sensor 320 or 520 in FIGS. 13-19 to be arranged on a circuit board and covered by a front cover.

Figure 13:
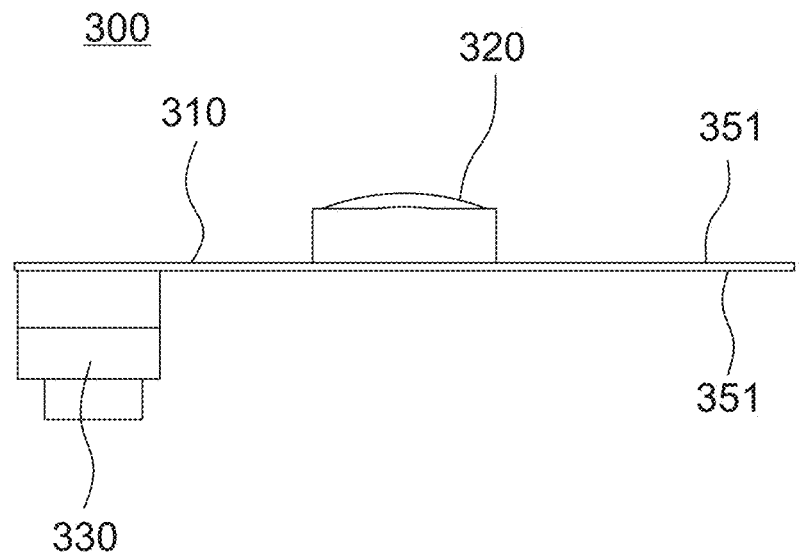
FIGS. 13 to 16 are schematic diagrams of an optical sensor assembly according to one embodiment of the present disclosure.
Figure 14:
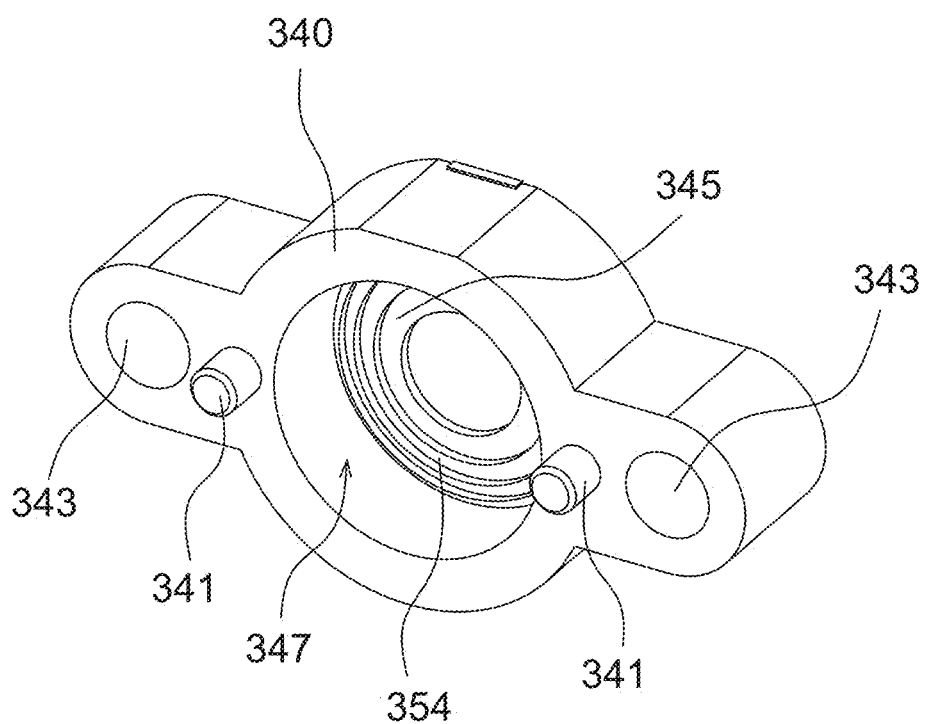
Figure 15:
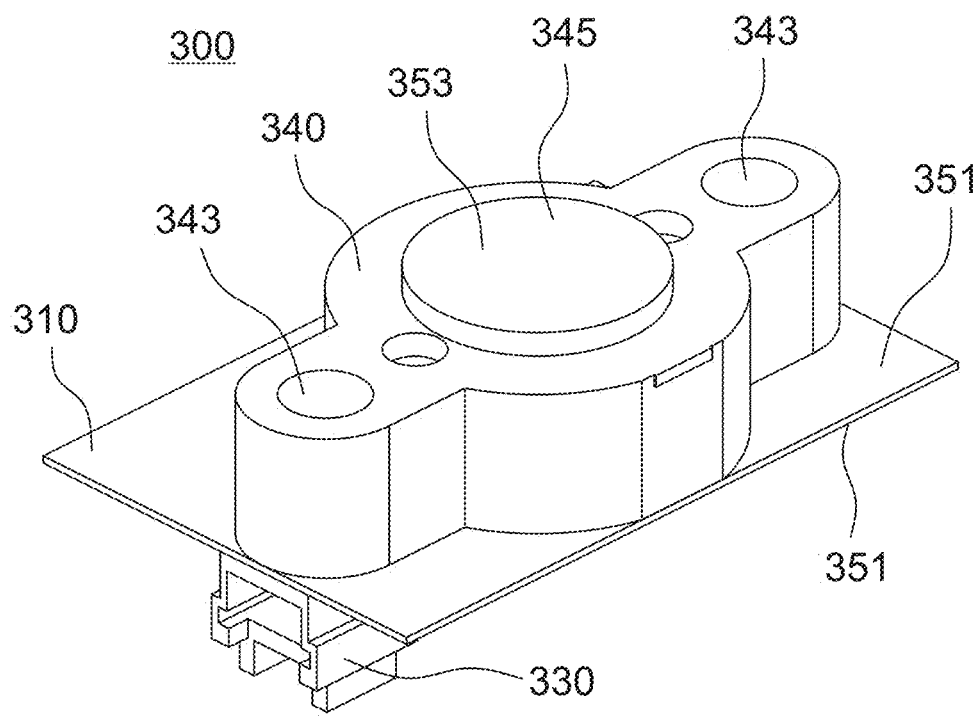
Figure 16:
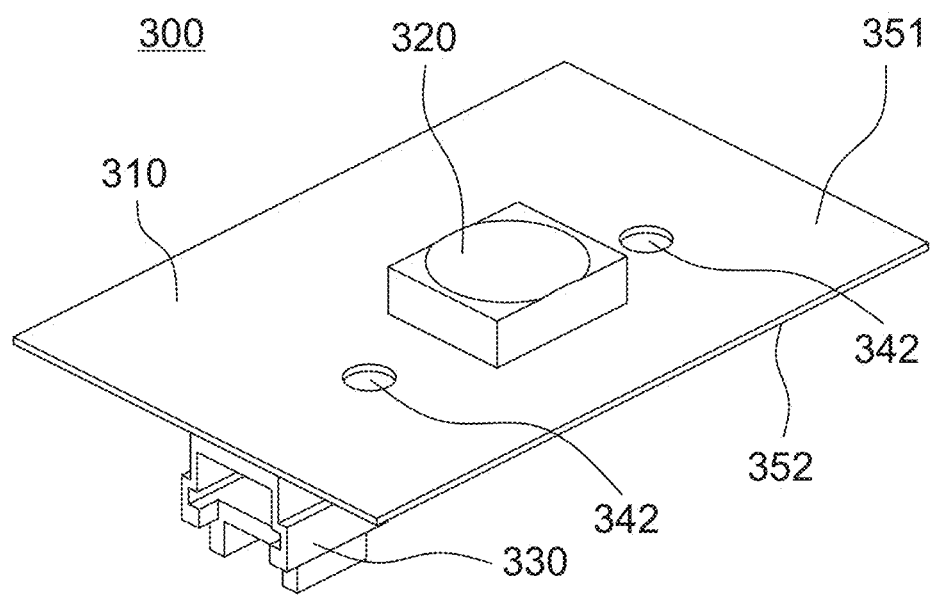

FIGS. 13, 14, 15 and 16 are schematic diagrams of an optical sensor assembly 300 according to one embodiment of the present disclosure. The optical sensor assembly 300 includes a circuit board 310 (e.g., a printed circuit board or a flexible circuit board), an optical sensor 320, a connector 330, and a front cover 340. FIG. 13 is a side view of the circuit board 310, the optical sensor 320, and the connector 330. FIG. 14 is a rear view of the front cover 340. FIG. 15 is a front view of the front cover 340 attached to the circuit board 310. FIG. 16 is another view of the circuit board 310 on which the front cover 340 is not yet attached. The connector 330 is attached to a back surface 352 of the circuit board 310, and the front cover 340 is attached to a front surface 351 of the circuit board 310.

The optical sensor 320 is positioned on and electrically connected to the circuit board 310. The connector 330 is positioned on the circuit board 310. The connector 330 is used to transmit electrical signals to and from the optical sensor 320. In addition, the connector 330 is used to transmit electrical signals between the optical sensor 320 and an external electronic device that adopts the optical sensor assembly 300. The front cover 340 is attached to the circuit board 310 and covers the optical sensor 320. The front cover 340 includes an optical element 345 used to allow incident light of a predetermined wavelength to transmit through the optical element 345 and condense the incident light onto the optical sensor 320. The optical element 345 is a convex lens or a Fresnel lens.

In one embodiment, an outer surface 353 of the optical element 345 is a plane surface, and the convex lens or the Fresnel lens is formed at an inner surface 354 of the optical element 345.

However, the present disclosure is not limited thereto. In one non-limiting aspect, the optical element 345 is a transparent layer used to guide incident light to the optical sensor 320 without condensing or diverging the incident light.

It should be mentioned that although FIG. 15 shows that the outer surface 353 of the optical element 345 is substantially parallel to the front surface 351 of the circuit board 310, the present disclosure is not limited thereto. According to an incident direction of the incident light, the outer surface 353 of the optical element 345 is preferably tilted to be perpendicular to the incident direction.

In one embodiment, the front cover 340, including the optical element 345, is made of polypropylene or polyethylene. The whole front cover 340, including the optical element 345, is produced via injection molding as a single piece. However, the present disclosure is not limited thereto. In one non-limiting aspect, the optical element 345 is formed separately from the front cover 340, and then squeezed into the front cover 340.

In another embodiment, the optical element 345 includes at least one of a polypropylene film, a polyethylene film, a silicon film, a germanium film, and a diamond-like carbon film.

In one embodiment, the optical sensor 320 is a far infra-red thermal sensor used to detect a temperature of a thermal source. The aforementioned predetermined wavelength of the incident light is in a range from 8 micrometers to 12 micrometers, and the optical element 345 is used to allow the incident light to transmit through the optical element 345 with a transmittance in a range from 20% to 80%.

In another embodiment, the optical sensor 320 is an ambient light sensor. The aforementioned predetermined wavelength of the incident light is in a range from 390 nanometers to 700 nanometers.

The optical sensor 320 generates electrical signals by detecting the incident light penetrating the optical element 345. The connector 330 transmits the electrical signals to a processor of an electronic device for predetermined control.

In one non-limiting aspect, the front cover 340 further includes at least one alignment peg 341 (e.g., two alignment pegs 341 being shown in FIG. 14), and the circuit board 310 includes at least one alignment hole 342 (e.g., two alignment hole 342 being shown in FIG. 15) used to receive the at least one alignment peg 341, and the at least one alignment peg 341 is formed integrally with the front cover 340. The front cover 340 further includes at least one screw hole 343 used to receive at least one screw for attaching and fixing the front cover 340 to the circuit board 310.

In the embodiment shown in FIGS. 14, 15 and 16, the front cover 340 includes two alignment pegs 341 and two screw holes 343, and the circuit board 310 includes two alignment holes 342. In another embodiment, the front cover 340 includes more or less alignment pegs 341 and more or less screw holes 343, and the circuit board 310 includes more or less alignment holes 342.

The front cover 340 further includes a receiving cavity 347 used to accommodate the optical sensor 320 attached on the circuit board 310. The front cover 340 is attached to the circuit board 310 via a water-proof and dust-proof adhesive, so that the circuit board 310, the adhesive, and the front cover 340 around the receiving cavity 347 form a sealed enclosure for accommodating and protecting the optical sensor 320 from various hazards of the ambient environment, such as water, dust, electrical damage and mechanical damage. In the aspect that the front cover 340 is combined with the circuit board 310 via adhesive, the at least one screw hole 343 is not implemented.

It should be mentioned that although the front cover 340 is shown to have curved edges between two protruding ends, it is only to illustrate but not to limit the present disclosure. In other embodiments, the front cover 340 has other shapes such as a rectangular shape according to a receiving opening of the electronic device adopting the optical sensor assembly 300.

Figure 17:
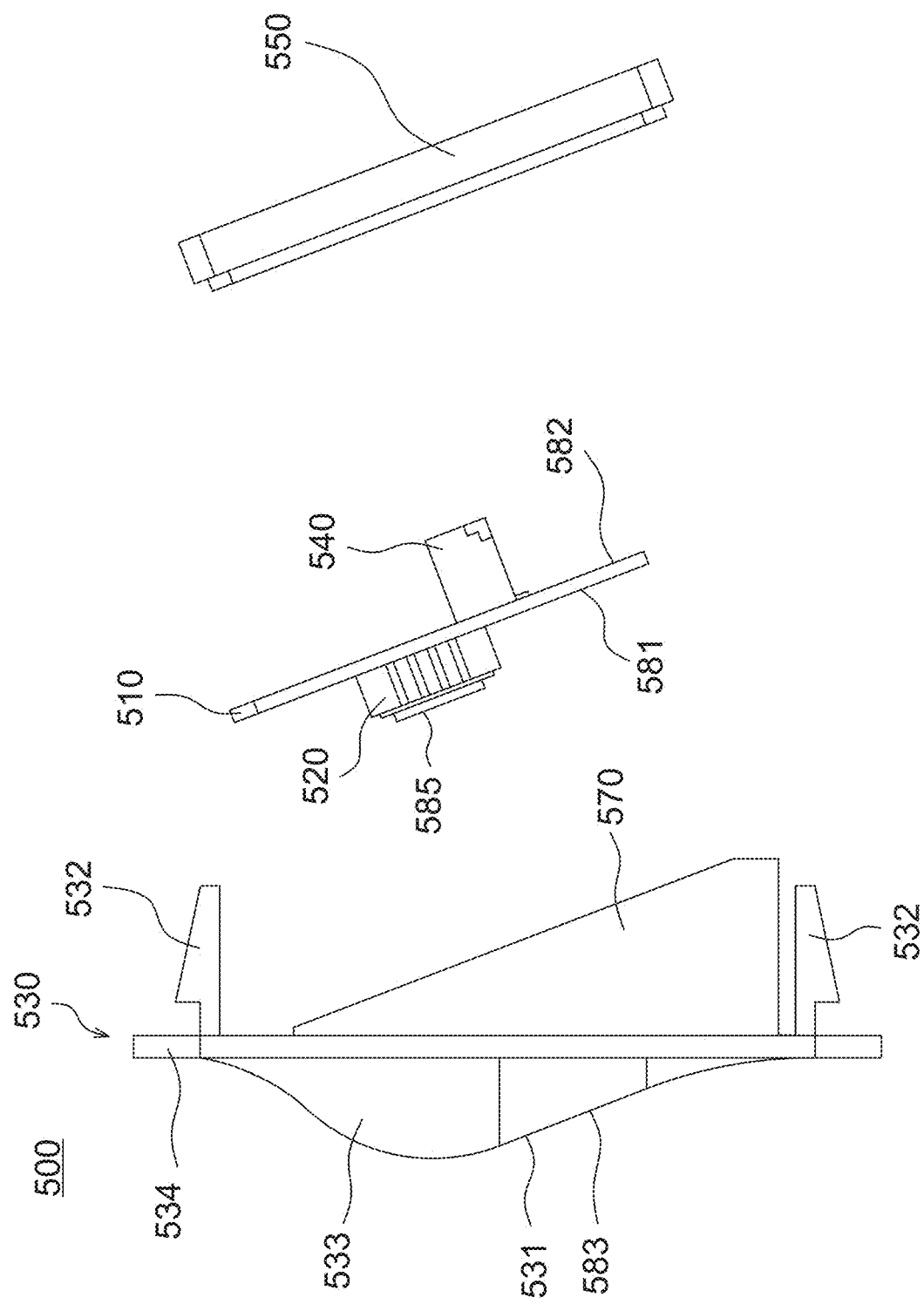
FIGS. 17 to 19 are schematic diagrams of an optical sensor assembly according to another embodiment of the present disclosure.
Figure 18:
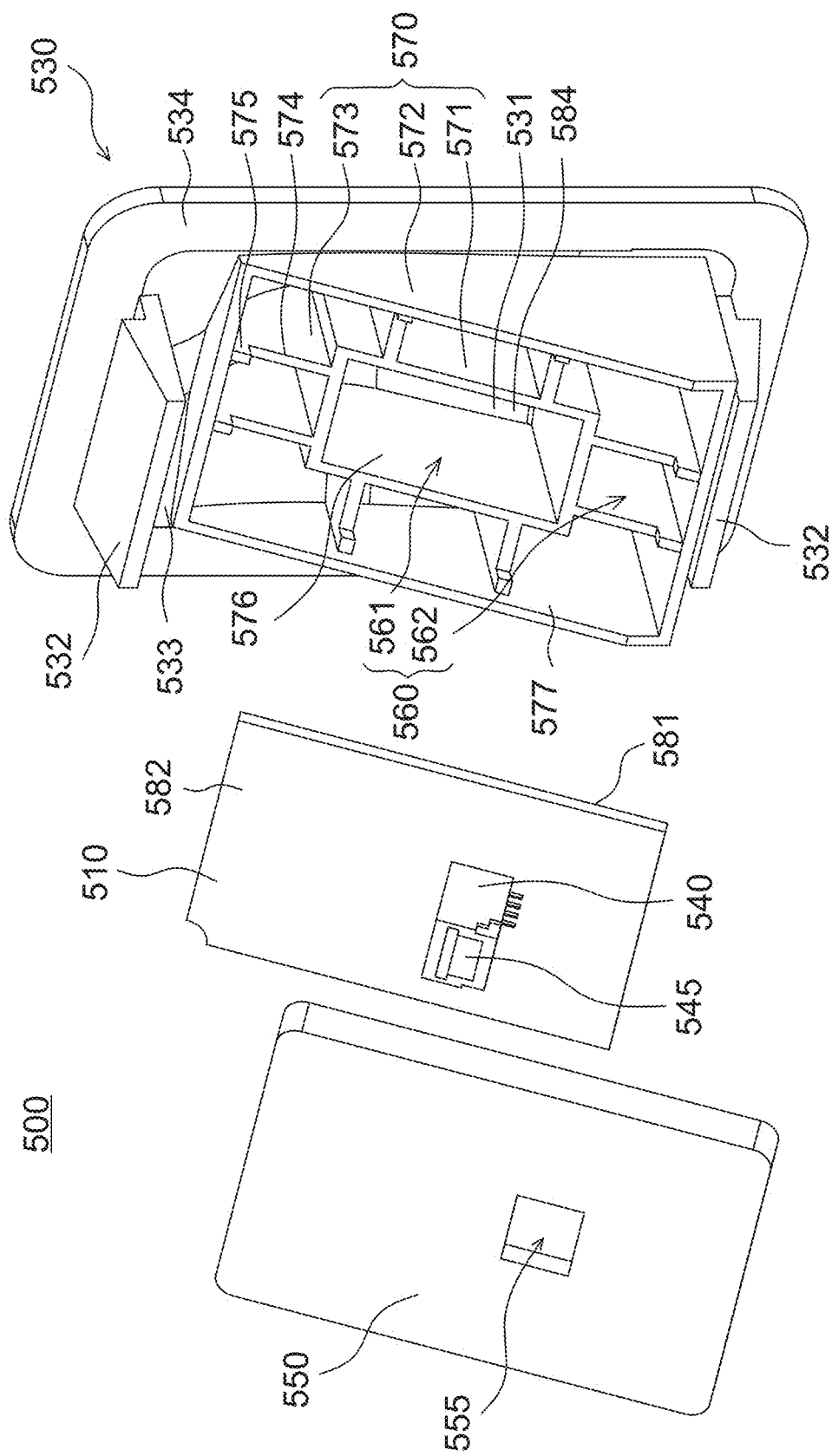
Figure 19:
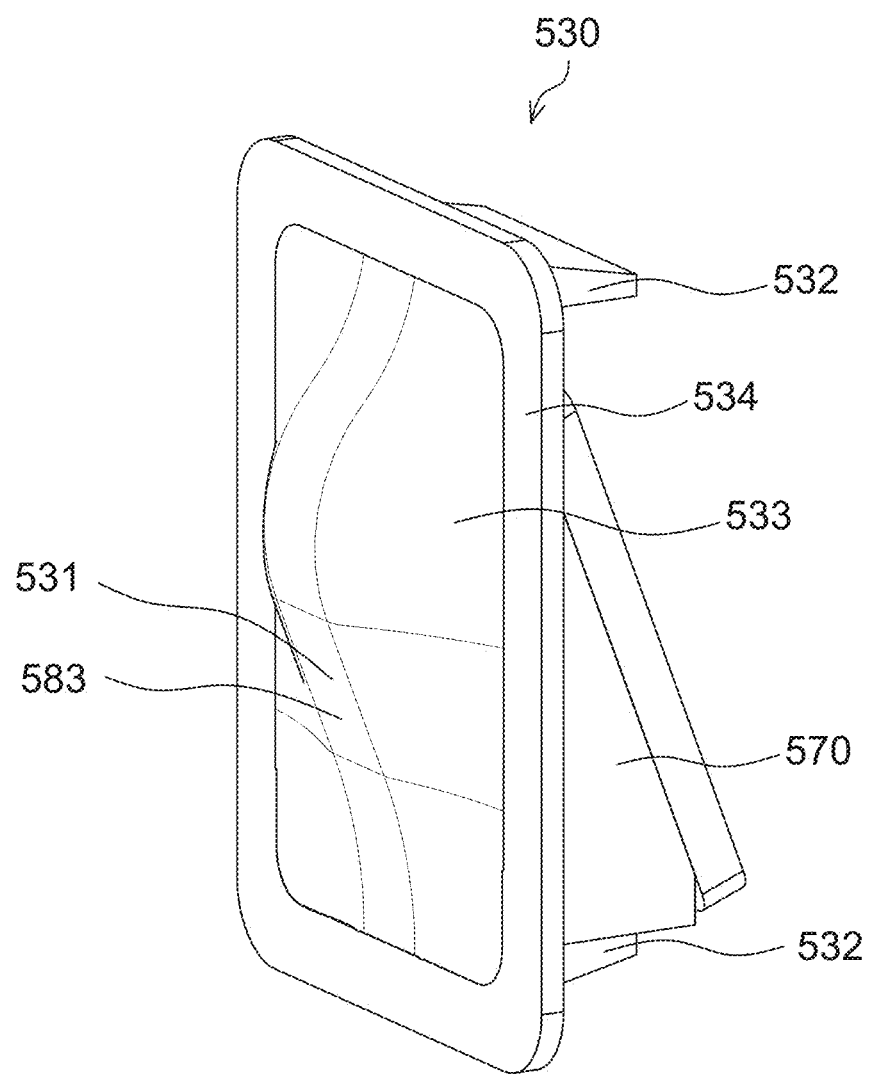

FIGS. 17, 18 and 19 are schematic diagrams of an optical sensor assembly 500 according to another embodiment of the present disclosure. The optical sensor assembly 500 includes a circuit board 510 (e.g., a printed circuit board or a flexible circuit board), an optical sensor 520, a connector 540, a front cover 530, and a back cover 550. FIG. 17 is a side view of the circuit board 510, the optical sensor 520, the connector 540, the front cover 530, and the back cover 550. FIG. 18 is a rear view of the circuit board 510, the connector 540, the front cover 530, and the back cover 550. FIG. 19 is a front view of the front cover 530.

In one non-limiting embodiment, when the circuit board 510 is fixed or sealed well with the front cover 530 to prevent dust and water from contacting the optical sensor 520, the back cover 550 is not implemented.

The optical sensor 520 is attached to a front surface 581 of the circuit board 510, and the optical sensor 520 is electrically connected with the circuit board 510. The front cover 530 includes a receiving cavity 560 used to receive at least the optical sensor 520. In one non-limiting embodiment, the receiving cavity 560 receives both the circuit board 510 and the optical sensor 520. The front cover 530 further includes an optical element 531 used to allow incident light of a predetermined wavelength to transmit through the optical element 531 and condense the incident light onto the optical sensor 520. The optical element 531 is a convex lens or a Fresnel lens.

In one embodiment, an outer surface 583 of the optical element 531 is a plane surface, and the convex lens or the Fresnel lens is formed at an inner surface 584 of the optical element 531.

However, the present disclosure is not limited thereto. In one non-limiting aspect, the optical element 531 is a transparent layer used to guide incident light to the optical sensor 520 without condensing or diverging the incident light.

In one embodiment, the optical sensor 520 is a far infra-red thermal sensor used to detect a temperature of a thermal source. The aforementioned predetermined wavelength of the incident light is in a range from 8 micrometers to 12 micrometers, and the optical element 531 is used to allow the incident light to transmit through the optical element 531 with a transmittance in a range from 20% to 80%.

In another embodiment, the optical sensor 520 is an ambient light sensor. The aforementioned predetermined wavelength of the incident light is in a range from 390 nanometers to 700 nanometers.

The front cover 530 further includes a curved sheet 533, a planar frame 535 connected to and surrounding the curved sheet 533, and a wall structure 570 positioned on the curved sheet 533. In another embodiment, the wall structure 570 is connected to the planar frame 535. The receiving cavity 560 is positioned in and formed by the wall structure 570. The optical element 531 is a part of the curved sheet 533. In one embodiment, the curved sheet 533 has a plane surface within a region of the optical element 531, and the rest part of the curved sheet 533 has a curved surface.

The optical sensor 520 is aligned with the optical element 531. Preferably, the optical element 531 is parallel to a sensing surface 585 of the optical sensor 520. In one aspect, the whole curved sheet 533 is transparent to the incident light. In another aspect, the curved sheet 533 is transparent to the incident light only within a region of the optical element 531, and the rest part of the curved sheet 533 is opaque or semi-opaque to the incident light.

In one embodiment, the optical element 531 and the optical sensor 520 are neither parallel nor perpendicular to the planar frame 535, as shown in FIG. 17. The angle difference between the planar frame 535 and the optical element 531 is determined based on design requirements of the optical sensor assembly 500.

In another embodiment, the optical element 531 and the optical sensor 520 are parallel to the planar frame 535. The optical element 531 is a part of the curved sheet 533. The circuit board 510 is attached to the wall structure 570. The shapes of the curved sheet 533 and the wall structure 570 are arranged such that the optical element 531, the optical sensor 520, and the circuit board 510 (determined by a tile angle of the outer loop wall 572) are all parallel. When the tile angle is changed, a light receiving angle of the optical element 531 and optical sensor 520 is also altered.

The wall structure 570 includes an inner loop wall 571 surrounding the optical element 531 and an outer loop wall 572 surrounding the inner loop wall 571. The inner loop wall 571 and the outer loop wall 572 have different heights at different edges of the front cover 530, e.g., lower at an upper edge and higher at a lower edge to cause the optical sensor 520 to have an angle difference with respect to the planar frame 535.

One end of the inner loop wall 571 is connected to the curved sheet 533 and another end of the inner loop wall 571 has an opening 576. One end of the outer loop wall 572 is connected to the curved sheet 533 and another end of the outer loop wall 572 has an opening 577. The area of the circuit board 510 is between the area of the opening 576 of the inner loop wall 571 and the area of the opening 577 of the outer loop wall 572. In other words, the area of the circuit board 510 is larger than the area of the opening 576 of the inner loop wall 571, and the area of the circuit board 510 is smaller than the area of the opening 577 of the outer loop wall 572 so as to be accommodated in the outer loop wall 572.

The receiving cavity 560 includes a first cavity 561 for receiving the optical sensor 520 and a second cavity 562 for receiving the circuit board 510. The first cavity 561 is positioned in the inner loop wall 571. The second cavity 562 is positioned in the outer loop wall 572.

To enhance the mechanical strength, the wall structure 570 further includes a plurality of ridge walls 573 connecting the inner loop wall 571, the outer loop wall 572 and the curved sheet 533. Each of the ridge walls 573 has an indent 574 on an edge 575 of that ridge wall 573 connecting the inner loop wall 571 and the outer loop wall 572. The second cavity 562 is formed by the indents 574 of all of the ridge walls 573.

In one non-limiting embodiment, the indents 574 and the second cavity 562 are not implemented. In this case, the circuit board 510 is attached to the inner loop wall 571 and the ridge walls 573 to seal the first cavity 561.

In one non-limiting embodiment, the ridge walls 573 are not implemented. In this case, the opening 577 of the outer loop wall 572 defines the second cavity 562.

In one non-limiting embodiment, the inner loop wall 571 is not implemented. In another one non-limiting embodiment, the outer loop wall 572 is not implemented. In another one non-limiting embodiment, both of the inner loop wall 571 and the outer loop wall 572 are not implemented.

According to FIG. 18, there are spaces between the ridge walls 573, the inner loop wall 571 and the outer loop wall 572. However, the present disclosure is not limited thereto. In one non-limiting embodiment, the ridge walls 573 fill all the spaces between the inner loop wall 571 and the outer loop wall 572 so that the wall structure 570 is a thick and solid loop wall surrounding the optical element 531 and the first cavity 561.

In one embodiment, the front cover 530, including the optical element 531, is made of polypropylene or polyethylene. The front cover 530, including the optical element 531 and the wall structure 570, is produced via injection molding as a single piece. However, the present disclosure is not limited thereto. In one non-limiting aspect, the optical element 531 is formed separately and has different materials from the front cover 530, and then combined with the front cover 530.

In another embodiment, the optical element 531 includes at least one of a polypropylene film, a polyethylene film, a silicon film, a germanium film, and a diamond-like carbon film.

The connector 540 is attached to a back surface 582 of the circuit board 510, and the connector 540 is electrically connected to the circuit board 510. The connector 540 is used to transmit electrical signals to and from the optical sensor 520. In addition, the connector 540 is used to transmit electrical signals between the optical sensor 520 and an external electronic device that adopts the optical sensor assembly 500. The back cover 550 is attached to the outer loop wall 572, for example, via a water-proof and dust-proof adhesive. The back cover 550 is used to seal the opening 577 of the outer loop wall 572. The back cover 550 has an opening 555 used to expose an end 545 of the connector 540.

The optical sensor 520 generates electrical signals by detecting the incident light penetrating the optical element 531. The connector 540 transmits the electrical signals to a processor of an electronic device for predetermined control.

In one embodiment, the circuit board 510 is attached to the inner loop wall 571 and the ridge walls 573, for example, via a water-proof and dust-proof adhesive. In this way, the circuit board 510, the inner loop wall 571, the curved sheet 533, and the optical element 531 form a sealed enclosure for accommodating and protecting the optical sensor 520 from various hazards of the ambient environment, such as water, dust, electrical damage and mechanical damage. The outer loop wall 572 and the back cover 550 provide additional protection for the optical sensor 520 against the hazards of the ambient environment.

In one embodiment, the optical sensor assembly 500 is applied to an electronic device. The front cover 530 further includes at least one latching hook 532 configured for attaching the optical sensor assembly 500 to the other parts of the electronic device. In the embodiment shown in FIGS. 17, 18 and 19, the front cover 530 includes two latching hooks 532. In another embodiment, the front cover 530 includes more or less latching hooks 532.

In one non-limiting embodiment, the optical sensor assembly 500 is attached to the electronic device by other means such as screws or adhesive, and the at least one latching hook 532 is not implemented.

It should be mentioned that although the front cover 530 is shown to have a rectangular appearance, it is only to illustrate but not to limit the present disclosure. In other embodiments, the front cover 530 has other shapes such as a circular or ellipse shape according to a receiving opening of the electronic device adopting the optical sensor assembly 500.

In the present disclosure, the type of the connector 330 and 540 is not particularly limited as long as it is combinable to another connector of an electronic device that adopts the optical sensor assembly 300 and 500.

As mentioned above, in an auto detection system, using an image sensor has a privacy concern and using a PIR motion sensor is unable to detect a steady object. Therefore, the present disclosure further provides an auto detection system using a thermopile sensor (FIG. 4) and operating methods thereof (FIGS. 8 and 10) that have broad applications such as the human detection in an elevator, the urine-wet detection, the stove detection, the hair temperature detection and the skin temperature detection.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An auto detection system, comprising:
a thermal detection device, having a field of view covering a pot on a stove, the thermal detection device comprising a thermopile sensor array configured to output a thermal frame having multiple object temperatures; and
a host, configured to receive the multiple object temperatures, and control an indication device to remind a user to put ingredients in the pot upon identifying that at least one of the multiple object temperatures is larger than a heating threshold.

2. The auto detection system as claimed in claim 1, wherein the host is further configured to
turn on an extraction fan upon identifying that the multiple object temperatures exceed a room temperature threshold, and
automatically adjust a wind strength of the extraction fan according to a variation of the multiple object temperatures exceeding the room temperature threshold.

3. The auto detection system as claimed in claim 1, wherein
the indication device is a display device, and
the host is further configured to inform the user to turn on an extraction fan via the display device upon identifying that the multiple object temperatures exceed a room temperature threshold.

4. The auto detection system as claimed in claim 1, wherein the host is further configured to control the indication device to indicate a warning message upon identifying that the multiple object temperatures exceed a high temperature threshold.

5. The auto detection system as claimed in claim 1, wherein
the indication device is a display device, and
the host is further configured to control the display device to show the multiple object temperatures as a 2D image.

6. The auto detection system as claimed in claim 1, wherein the host is further configured to switch off the stove when there is no human body moving in the field of view for a predetermined time interval.

7. An auto detection system, comprising:
a thermal detection device, having a field of view covering ingredients, the thermal detection device comprising a thermopile sensor array configured to output a thermal frame having multiple object temperatures; and
a host, configured to receive the multiple object temperatures, and control an indication device to remind a user to turn over the ingredients upon identifying that uniformity of the multiple object temperatures is lower than a uniformity threshold.

8. The auto detection system as claimed in claim 7, wherein the host is further configured to
turn on an extraction fan upon identifying that the multiple object temperatures exceed a room temperature threshold, and
automatically adjust a wind strength of the extraction fan according to a variation of the multiple object temperatures exceeding the room temperature threshold.

9. The auto detection system as claimed in claim 7, wherein
the indication device is a display device, and
the host is further configured to inform the user to turn on an extraction fan via the display device upon identifying that the multiple object temperatures exceed a room temperature threshold.

10. The auto detection system as claimed in claim 7, wherein the host is further configured to control the indication device to indicate a warning message upon identifying that the multiple object temperatures exceed a high temperature threshold.

11. The auto detection system as claimed in claim 7, wherein
the indication device is a display device, and
the host is further configured to control the display device to show the multiple object temperatures as a 2D image.

12. The auto detection system as claimed in claim 7, wherein the host is further configured to switch off a stove containing the ingredients when there is no human body moving in the field of view for a predetermined time interval.

* * * * *